US009858776B1

(12) United States Patent
Busby et al.

(10) Patent No.: US 9,858,776 B1
(45) Date of Patent: Jan. 2, 2018

(54) TAMPER-RESPONDENT ASSEMBLY WITH NONLINEARITY MONITORING

(71) Applicant: INTERNATIONAL BUSINESS MACHINES CORPORATION, Armonk, NY (US)

(72) Inventors: James A. Busby, New Paltz, NY (US); Phillip Duane Isaacs, Rochester, MN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/194,738

(22) Filed: Jun. 28, 2016

(51) Int. Cl.
| G08B 13/08 | (2006.01) |
| G08B 13/12 | (2006.01) |
| H05K 1/18 | (2006.01) |
| H05K 1/02 | (2006.01) |
| G01N 27/20 | (2006.01) |

(52) U.S. Cl.
CPC ......... G08B 13/128 (2013.01); G01N 27/205 (2013.01); H05K 1/0275 (2013.01); H05K 1/0296 (2013.01); H05K 1/182 (2013.01); H05K 2201/10151 (2013.01)

(58) Field of Classification Search
CPC ............................ G08B 21/18; G08B 13/1418
USPC ... 340/545.6, 10.1, 10.6, 505, 506, 508, 509
See application file for complete search history.

(56) References Cited

U.S. PATENT DOCUMENTS

| 3,165,569 A | 1/1965 | Bright et al. |
| 4,160,503 A | 7/1979 | Ohlbach |
| 4,211,324 A | 7/1980 | Ohlbach |
| 4,324,823 A | 4/1982 | Ray, III |
| 4,496,900 A | 1/1985 | Di Stefano et al. |
| 4,516,679 A | 5/1985 | Simpson |

(Continued)

FOREIGN PATENT DOCUMENTS

| CN | 2014-30639 Y | 3/2010 |
| CN | 10-4346587 A | 2/2015 |

(Continued)

OTHER PUBLICATIONS

Holm, Ragnar, "Electric Contacts: Theory and Application", Spinger-Verlag, New York, 4th Edition, 1981 (pp. 10-19).

(Continued)

*Primary Examiner* — Tai T Nguyen
(74) *Attorney, Agent, or Firm* — Teddi Maranzano; Kevin P. Radigan, Esq.; Heslin, Rothenberg, Farley & Mesiti

(57) ABSTRACT

Tamper-respondent assemblies and methods of fabrication are provided which include at least one tamper-respondent sensor and a detector. The at least one tamper-respondent sensor includes conductive lines which form, at least in part, at least one tamper-detect network of the tamper-respondent sensor(s). The detector monitors the tamper-respondent sensor(s) by applying an electrical signal to the conductive lines of the at least one tamper-respondent sensor to monitor for a non-linear conductivity change indicative of a tamper event at the tamper-respondent sensor(s). For instance, the detector may monitor a second harmonic of the electrical signal applied to the conductive lines for the non-linear conductivity change indicative of the tamper event, such as an attempted shunt of one or more conductive lines of the tamper-respondent sensor(s).

17 Claims, 11 Drawing Sheets

(56) References Cited

U.S. PATENT DOCUMENTS

| | | |
|---|---|---|
| 4,593,384 A | 6/1986 | Kleijne |
| 4,609,104 A | 9/1986 | Kasper et al. |
| 4,653,252 A | 3/1987 | Van de Haar et al. |
| 4,677,809 A | 7/1987 | Long et al. |
| 4,691,350 A | 9/1987 | Kleijne et al. |
| 4,807,284 A | 2/1989 | Kleijne |
| 4,811,288 A | 3/1989 | Kleijne et al. |
| 4,860,351 A | 8/1989 | Weingart |
| 4,865,197 A | 9/1989 | Craig |
| 5,009,311 A | 4/1991 | Schenk |
| 5,027,397 A | 6/1991 | Double et al. |
| 5,060,114 A | 10/1991 | Feinberg et al. |
| 5,075,822 A | 12/1991 | Baumler et al. |
| 5,117,457 A | 5/1992 | Comerford et al. |
| 5,159,629 A | 10/1992 | Double et al. |
| 5,185,717 A | 2/1993 | Mori |
| 5,201,868 A | 4/1993 | Johnson |
| 5,201,879 A | 4/1993 | Steele et al. |
| 5,211,618 A | 5/1993 | Stoltz |
| 5,239,664 A | 8/1993 | Verrier et al. |
| 5,389,738 A | 2/1995 | Piosenka et al. |
| 5,406,630 A | 4/1995 | Piosenka et al. |
| 5,506,566 A | 4/1996 | Oldfield et al. |
| 5,568,124 A | 10/1996 | Joyce et al. |
| 5,594,439 A | 1/1997 | Swanson |
| 5,675,319 A | 10/1997 | Rivenberg et al. |
| 5,715,652 A | 2/1998 | Stahlecker |
| 5,761,054 A | 6/1998 | Kuhn |
| 5,813,113 A | 9/1998 | Stewart et al. |
| 5,858,500 A | 1/1999 | MacPherson |
| 5,880,523 A | 3/1999 | Candelore |
| 5,988,510 A | 11/1999 | Tuttle et al. |
| 6,121,544 A | 9/2000 | Petsinger |
| 6,195,267 B1 | 2/2001 | MacDonald, Jr. et al. |
| 6,201,296 B1 | 3/2001 | Fries et al. |
| 6,259,363 B1 * | 7/2001 | Payne ............... G08B 29/043 340/505 |
| 6,261,215 B1 | 7/2001 | Imer |
| 6,301,096 B1 | 10/2001 | Wozniczka |
| 6,384,397 B1 | 5/2002 | Takiar et al. |
| 6,420,971 B1 * | 7/2002 | Leck ............... E05B 39/04 340/542 |
| 6,424,954 B1 | 7/2002 | Leon |
| 6,438,825 B1 | 8/2002 | Kuhm |
| 6,469,625 B1 | 10/2002 | Tomooka |
| 6,512,454 B2 | 1/2003 | Miglioli et al. |
| 6,643,995 B1 | 11/2003 | Koyama et al. |
| 6,686,539 B2 | 2/2004 | Farquhar et al. |
| 6,746,960 B2 | 6/2004 | Goodman et al. |
| 6,798,660 B2 | 9/2004 | Moss et al. |
| 6,853,093 B2 | 2/2005 | Cohen et al. |
| 6,879,032 B2 | 4/2005 | Rosenau et al. |
| 6,929,900 B2 | 8/2005 | Farquhar et al. |
| 6,946,960 B2 | 9/2005 | Sisson et al. |
| 6,957,345 B2 | 10/2005 | Cesana et al. |
| 6,970,360 B2 | 11/2005 | Sinha |
| 6,985,362 B2 | 1/2006 | Mori et al. |
| 6,991,961 B2 | 1/2006 | Hubbard et al. |
| 6,996,953 B2 | 2/2006 | Perreault et al. |
| 7,005,733 B2 | 2/2006 | Kommerling et al. |
| 7,015,823 B1 | 3/2006 | Gillen et al. |
| 7,054,162 B2 | 5/2006 | Benson et al. |
| 7,057,896 B2 | 6/2006 | Matsuo et al. |
| 7,094,143 B2 | 8/2006 | Wolm et al. |
| 7,094,459 B2 | 8/2006 | Takahashi |
| 7,095,615 B2 | 8/2006 | Nichols |
| 7,156,233 B2 | 1/2007 | Clark et al. |
| 7,180,008 B2 | 2/2007 | Heitmann et al. |
| 7,189,360 B1 | 3/2007 | Ho et al. |
| 7,214,874 B2 | 5/2007 | Dangler et al. |
| 7,247,791 B2 | 7/2007 | Kulpa |
| 7,304,373 B2 | 12/2007 | Taggart et al. |
| 7,310,737 B2 | 12/2007 | Patel et al. |
| 7,465,887 B2 | 12/2008 | Suzuki et al. |
| 7,475,474 B2 | 1/2009 | Heitmann et al. |
| 7,515,418 B2 | 4/2009 | Straznicky et al. |
| 7,549,064 B2 | 6/2009 | Elbert et al. |
| 7,640,658 B1 | 1/2010 | Pham et al. |
| 7,643,290 B1 | 1/2010 | Narasimhan et al. |
| 7,663,883 B2 | 2/2010 | Shirakami et al. |
| 7,672,129 B1 | 3/2010 | Ouyang et al. |
| 7,731,517 B2 | 6/2010 | Lee et al. |
| 7,746,657 B2 | 6/2010 | Oprea et al. |
| 7,760,086 B2 | 7/2010 | Hunter et al. |
| 7,768,005 B2 | 8/2010 | Condorelli et al. |
| 7,783,994 B2 | 8/2010 | Ball et al. |
| 7,787,256 B2 | 8/2010 | Chan et al. |
| 7,868,441 B2 | 1/2011 | Eaton et al. |
| 7,898,413 B2 | 3/2011 | Hsu et al. |
| 7,901,977 B1 | 3/2011 | Angelopoulos et al. |
| 7,947,911 B1 | 5/2011 | Pham et al. |
| 7,978,070 B2 | 7/2011 | Hunter |
| 8,084,855 B2 | 12/2011 | Lower et al. |
| 8,094,450 B2 | 1/2012 | Cole et al. |
| 8,133,621 B2 | 3/2012 | Wormald et al. |
| 8,199,506 B2 | 6/2012 | Janik et al. |
| 8,201,267 B2 | 6/2012 | Moh et al. |
| 8,287,336 B2 | 10/2012 | Dangler et al. |
| 8,325,486 B2 | 12/2012 | Arshad et al. |
| 8,516,269 B1 | 8/2013 | Hamlet et al. |
| 8,589,703 B2 | 11/2013 | Lee et al. |
| 8,646,108 B2 | 2/2014 | Shiakallis et al. |
| 8,659,506 B2 | 2/2014 | Nomizo |
| 8,659,908 B2 | 2/2014 | Adams et al. |
| 8,664,047 B2 | 3/2014 | Lower et al. |
| 8,716,606 B2 | 5/2014 | Kelley et al. |
| 8,797,059 B2 | 8/2014 | Boday et al. |
| 8,836,509 B2 | 9/2014 | Lowy |
| 8,853,839 B2 | 10/2014 | Gao et al. |
| 8,879,266 B2 | 11/2014 | Jarvis et al. |
| 8,890,298 B2 | 11/2014 | Buer et al. |
| 8,947,889 B2 | 2/2015 | Kelley et al. |
| 8,961,280 B2 | 2/2015 | Dangler et al. |
| 9,003,199 B2 | 4/2015 | Dellmo et al. |
| 9,011,762 B2 | 4/2015 | Seppa et al. |
| 9,052,070 B2 | 6/2015 | Davis et al. |
| 9,166,586 B2 | 10/2015 | Carapelli et al. |
| 9,298,956 B2 | 3/2016 | Wade et al. |
| 2001/0050425 A1 | 12/2001 | Beroz et al. |
| 2001/0056542 A1 | 12/2001 | Cesana et al. |
| 2002/0002683 A1 | 1/2002 | Benson |
| 2002/0068384 A1 | 6/2002 | Beroz et al. |
| 2002/0084090 A1 | 7/2002 | Farquhar |
| 2003/0009684 A1 | 1/2003 | Schwenck et al. |
| 2005/0068735 A1 | 3/2005 | Fissore et al. |
| 2005/0111194 A1 | 5/2005 | Sohn et al. |
| 2005/0180104 A1 | 8/2005 | Olesen et al. |
| 2006/0034731 A1 | 2/2006 | Lewis et al. |
| 2006/0072288 A1 | 4/2006 | Stewart et al. |
| 2006/0196945 A1 | 9/2006 | Mendels |
| 2006/0218779 A1 | 10/2006 | Ooba et al. |
| 2007/0064396 A1 | 3/2007 | Oman et al. |
| 2007/0064399 A1 | 3/2007 | Mandel et al. |
| 2007/0108619 A1 | 5/2007 | Hsu |
| 2007/0211436 A1 | 9/2007 | Robinson et al. |
| 2007/0223165 A1 * | 9/2007 | Itri ............... H04M 3/18 361/115 |
| 2007/0230127 A1 | 10/2007 | Peugh et al. |
| 2007/0268714 A1 | 11/2007 | Brandenburg et al. |
| 2008/0050512 A1 | 2/2008 | Lower et al. |
| 2008/0106400 A1 * | 5/2008 | Hunter ............... G06F 21/87 340/540 |
| 2008/0144290 A1 | 6/2008 | Brandt et al. |
| 2008/0159539 A1 | 7/2008 | Huang et al. |
| 2008/0160274 A1 | 7/2008 | Dang et al. |
| 2008/0191174 A1 | 8/2008 | Ehrensvard et al. |
| 2008/0251906 A1 | 10/2008 | Eaton et al. |
| 2009/0073659 A1 | 3/2009 | Peng et al. |
| 2009/0166065 A1 | 7/2009 | Clayton et al. |
| 2010/0088528 A1 | 4/2010 | Sion |
| 2010/0110647 A1 | 5/2010 | Hiew et al. |
| 2010/0177487 A1 | 7/2010 | Arshad et al. |

(56) References Cited

U.S. PATENT DOCUMENTS

| | | |
|---|---|---|
| 2010/0319986 A1 | 12/2010 | Bleau et al. |
| 2011/0001237 A1 | 1/2011 | Brun et al. |
| 2011/0038123 A1 | 2/2011 | Janik et al. |
| 2011/0103027 A1 | 5/2011 | Aoki et al. |
| 2011/0241446 A1 | 10/2011 | Tucholski |
| 2011/0299244 A1 | 12/2011 | Dede et al. |
| 2012/0050998 A1 | 3/2012 | Klum et al. |
| 2012/0117666 A1 | 5/2012 | Oggioni et al. |
| 2012/0140421 A1 | 6/2012 | Kirstine et al. |
| 2012/0319986 A1 | 6/2012 | Toh et al. |
| 2012/0170217 A1 | 7/2012 | Nishikimi et al. |
| 2012/0185636 A1 | 7/2012 | Leon et al. |
| 2012/0244742 A1 | 9/2012 | Wertz et al. |
| 2012/0256305 A1 | 10/2012 | Kaufmann et al. |
| 2012/0320529 A1 | 12/2012 | Loong et al. |
| 2013/0033818 A1 | 2/2013 | Hosoda et al. |
| 2013/0104252 A1 | 4/2013 | Yanamadala et al. |
| 2013/0141137 A1 | 6/2013 | Krutzik et al. |
| 2013/0158936 A1 | 6/2013 | Rich et al. |
| 2013/0208422 A1 | 8/2013 | Hughes et al. |
| 2013/0235527 A1 | 9/2013 | Wagner et al. |
| 2013/0283386 A1* | 10/2013 | Lee .................. G06F 21/86 726/26 |
| 2014/0022733 A1 | 1/2014 | Lim et al. |
| 2014/0160679 A1 | 6/2014 | Kelty et al. |
| 2014/0184263 A1 | 7/2014 | Ehrenpfordt et al. |
| 2014/0204533 A1 | 7/2014 | Abeyasekera et al. |
| 2014/0321064 A1 | 10/2014 | Bose et al. |
| 2014/0325688 A1 | 10/2014 | Cashin et al. |
| 2015/0007427 A1 | 1/2015 | Dangler et al. |
| 2015/0235053 A1 | 8/2015 | Lee et al. |
| 2016/0005262 A1 | 1/2016 | Hirato et al. |
| 2016/0012693 A1* | 1/2016 | Sugar .................. G08B 13/1409 340/568.3 |
| 2016/0137548 A1 | 5/2016 | Cabral, Jr. et al. |
| 2016/0262253 A1 | 9/2016 | Isaacs et al. |
| 2016/0262270 A1 | 9/2016 | Isaacs et al. |
| 2017/0019987 A1 | 1/2017 | Dragone et al. |

FOREIGN PATENT DOCUMENTS

| | | |
|---|---|---|
| DE | 19816571 A1 | 10/1999 |
| DE | 19816572 A1 | 10/1999 |
| DE | 10-2012-203955 A1 | 9/2013 |
| EP | 0 056 360 A1 | 10/1993 |
| EP | 0 629 497 A2 | 12/1994 |
| EP | 1 184 773 A1 | 3/2002 |
| EP | 1 207 444 A2 | 5/2002 |
| EP | 1 734 578 A1 | 12/2006 |
| EP | 1 968 362 A2 | 9/2008 |
| EP | 2 104 407 A1 | 9/2009 |
| EP | 1 672 464 B1 | 4/2012 |
| EP | 2 560 467 A1 | 2/2013 |
| JP | 61-297035 A | 12/1986 |
| JP | 2000-238141 A | 9/2000 |
| JP | 2013-125807 A | 6/2013 |
| JP | 2013-140112 A | 7/2013 |
| WO | WO 99/03675 A1 | 1/1999 |
| WO | WO 99/21142 A1 | 4/1999 |
| WO | WO 01/63994 A2 | 8/2001 |
| WO | 03/012606 A2 | 2/2003 |
| WO | WO 03/025080 A1 | 3/2003 |
| WO | WO 2004/040505 A1 | 5/2004 |
| WO | WO 2009/042335 A1 | 4/2009 |
| WO | WO 2009/092472 A1 | 7/2009 |
| WO | WO 2010/128939 A1 | 11/2010 |
| WO | WO 2013/004292 A1 | 1/2013 |
| WO | WO 2013/0189483 A1 | 12/2013 |
| WO | WO 2014/086987 A2 | 6/2014 |
| WO | WO 2014/158159 A1 | 10/2014 |

OTHER PUBLICATIONS

Clark, Andrew J., "Physical Protection of Cryptographic Devices", Advanced in Cyprtology, Eurocrypt '87, Springer, Berlin Heidelberg (1987) (11 pages).

Halperin et al., "Latent Open Testing of Electronic Packaging", MCMC-194, IEEE (1994) (pp. 83-33).

Simek, Bob, "Tamper Restrictive Thermal Ventilation System for Enclosures Requiring Ventilation and Physical Security", IBM Publication No. IPCOM000008607D, Mar. 1, 1998 (2 pages).

Pamula et al., "Cooling of Integrated Circuits Using Droplet-Based Microfluidics", Association for Computing Machinery (ACM), GLSVLSI'03, Apr. 28-29, 2003 (pp. 84-87).

Saran et al., "Fabrication and Characterization of Thin Films of Single-Walled Carbon Nanotube Bundles on Flexible Plastic Substrates", Journal of the American Chemical Society, vol. 126, No. 14 (Mar. 23, 2004) (pp. 4462-4463).

Khanna P.K. et al., "Studies on Three-Dimensional Moulding, Bonding and Assembling of Low-Temperature-Cofired Ceramics MEMS and MST Applications." Materials Chemistry and Physics, vol. 89, No. 1 (2005) (pp. 72-79).

Drimer et al., "Thinking Inside the Box: System-Level Failures of Tamper Proofing", 2008 IEEE Symposium on Security and Privacy, (Feb. 2008) (pp. 281-295).

Loher et al., "Highly Integrated Flexible Electronic Circuits and Modules", 3rd International IEEE on Microsystems, Packaging, Assembly & Circuits Technology Conference (Oct. 22-24, 2008) (Abstract Only) (1 page).

Sample et al., "Design of an RFID-Based Battery-Free Programmable Sensing Platform", IEEE Transactions on Instrumentation and Measurement, vol. 57, No. 11, Nov. 2008 (pp. 2608-2615).

Jhang et al., "Nonlinear Ultrasonic Techniques for Non-Destructive Assessment of Micro Damage in Material: A Review", International Journal of Prec. Eng. & Manuf, vol. 10, No. 1, Jan. 2009 (pp. 123-135).

Anonymous, "Consolidated Non-Volatile Memory in a Chip Stack", IBM Technical Disclosure: IP.com No. IPCOM000185250, Jul. 16, 2009 (6 pages).

Isaacs et al., "Tamper Proof, Tamper Evident Encryption Technology", Pan Pacific Symposium SMTA Proceedings (2013) (9 pages).

Anonymous, "Selective Memory Encryption", IBM Technical Disclosure: IP.com IPCOM000244183, Nov. 20, 2015 (6 pages).

Zhou et al., "Nonlinear Analysis for Hardware Trojan Detection", ICSPCC2015, IEEE (2015) (4 pages).

Dangler et al., "Tamper-Respondent Sensors with Formed Flexible Layer(s)", U.S. Appl. No. 14/865,551, filed Sep. 25, 2015 (113 pages).

Brodsky et al., "Overlapping, Discrete Tamper-Respondent Sensors", U.S. Appl. No. 14/865,572, filed Sep. 25, 2015 (114 pages).

Dangler et al., "Tamper-Respondent Assemblies with Region(s) of Increased Susceptibility to Damage", U.S. Appl. No. 14/865,591, filed Sep. 25, 2015 (114 pages).

Brodsky et al., "Circuit Boards and Electronic Packages with Embedded Tamper-Respondent Sensor", U.S. Appl. No. 14/865,610, filed Sep. 25, 2015 (43 pages).

Brodsky et al, "Tamper-Respondent Assemblies", U.S. Appl. No. 14/865,632, filed Sep. 25, 2015 (115 pages).

Brodksky et al., "Enclosure with Inner Tamper-Respondent Sensor(s)", U.S. Appl. No. 14/865,651, filed Sep. 25, 2015 (115 pages).

Fisher et al., "Enclosure with Inner Tamper-Respondent Sensor(s) and Physical Security Element(s)", U.S. Appl. No. 14/865,686, filed Sep. 25, 2015 (114 pages).

Brodsky et al., "Tamper-Respondent Assemblies with Bond Protection", U.S. Appl. No. 14/865,708, filed Sep. 25, 2015 (113 pages).

Brodsky et al., "Circuit Layouts of Tamper-Respondent Sensors", U.S. Appl. No. 14/886,179, filed Oct. 19, 2015 (113 pages).

Isaacs, Phillip Duane, "Tamper-Respondent Assembly with Protective Wrap(s) Over Tamper-Respondent Sensor(s)", U.S. Appl. No. 14/918,691, filed Oct. 21, 2015 (40 pages).

Brodsky et al., "Tamper-Respondent Assemblies with Bond Protection", U.S. Appl. No. 14/941,860, filed Nov. 16, 2015 (108 pages).

Fisher et al., "Enclosure with Inner Tamper-Respondent Sensor(s) and Physical Security Element(s)", U.S. Appl. No. 14/941,872, filed Nov. 16, 2015 (109 pages).

(56) References Cited

OTHER PUBLICATIONS

Brodsky et al, "Tamper-Respondent Assemblies", U.S. Appl. No. 14/941,887, filed Nov. 16, 2015 (109 pages).
Brodsky et al., "Circuit Boards and Electronic Packages with Embedded Tamper-Respondent Sensors", U.S. Appl. No. 14/941,908, filed Nov. 16, 2015 (41 pages).
Fisher et al., "Tamper-Respondent Assembly with Vent Structure", U.S. Appl. No. 14/955,283, filed Dec. 1, 2015 (61 pages).
Fisher et al., "Applying Pressure to Adhesive Using CTE Mismatch Between Components", U.S. Appl. No. 14/963,681, filed Dec. 9, 2015 (68 pages).
Brodsky et al., "Tamper-Respondent Assemblies with Enclosure-to-Board Protection", U.S. Appl. No. 14/974,036, filed Dec. 18, 2015 (55 pages).
Busby et al., "Multi-Layer Stack with Embedded Tamper-Detect Protection", U.S. Appl. No. 15/053,336, filed Feb. 25, 2016 (68 pages).
Campbell et al., "Tamper-Proof Electronic Packages With Two-Phase Dielectric Fluid", U.S. Appl. No. 15/139,503, filed Apr. 27, 2016 (60 pages).
Busby et al., "Tamper-Proof Electronic Packages Formed With Stressed Glass", U.S. Appl. No. 15/154,077, filed May 13, 2016 (45 pages).
Busby et al., "Tamper-Proof Electronic Packages With Stressed Glass Component Substrate(s)", U.S. Appl. No. 15/154,088, filed May 13, 2016 (56 pages).
Brodsky et al., "Circuit Layouts of Tamper-Respondent Sensors", U.S. Appl. No. 15/187,002, filed Jun. 20, 2016 (110 pages).
Brodsky et al., "Tamper-Respondent Assemblies with Enclosure-to-Board Protection", U.S. Appl. No. 15/193,525, filed Jun. 27, 2016 (54 pages).
Fisher et al., "Applying Pressure to Adhesive Using CTE Mismatch Between Components", U.S. Appl. No. 15/193,556, filed Jun. 27, 2016 (71 pages).
Dangler et al., "Tamper-Respondent Sensors with Formed Flexible Layer(s)", U.S. Appl. No. 15/249,663, filed Aug. 29, 2016 (109 pages).
Brodsky et al., "Overlapping, Discrete Tamper-Respondent Sensors", U.S. Appl. No. 15/249,671, filed Aug. 29, 2016 (109 pages).
Dangler et al., "Tamper-Respondent Assemblies with Region(s) of Increased Susceptibility to Damage", U.S. Appl. No. 15/249,676, filed Aug. 29, 2016 (110 pages).
Isaacs et al., Office Action for U.S. Appl. No. 14/637,501, filed Mar. 4, 2015, dated May 4, 2016 (20 pages).
Fisher et al., Office Action for U.S. Appl. No. 14/963,681, filed Dec. 9, 2015, dated May 6, 2016 (10 pages).
Brodsky et al., Notice of Allowance for U.S. Appl. No. 14/974,036, filed Dec. 18, 2015, dated Jun. 3, 2016 (18 pages).
Fisher et al., Office Action for U.S. Appl. No. 14/865,686, filed Sep. 25, 2015, dated Jun. 29, 2016 (17 pages).
Fisher et al., Notice of Allowance for U.S. Appl. No. 14/963,681, filed Dec. 9, 2015, dated Jul. 5, 2016 (7 pages).
Brodsky et al., Office Action for U.S. Appl. No. 14/865,651, filed Sep. 25, 2015, dated Jul. 13, 2016 (10 pages).
Dragone et al., "Tamper-Respondent Assembly with Sensor Connection Adapter", U.S. Appl. No. 15/268,959, filed Sep. 19, 2016 (45 pages).
Dragone et al., "Vented Tamper-Respondent Assemblies", U.S. Appl. No. 15/275,748, filed Sep. 26, 2016 (53 pages).
Dragone et al., "Tamper-Respondent Assemblies with in Situ Vent Structure(s)", U.S. Appl. No. 15/275,762, filed Sep. 26, 2016 (72 pages).
Busby et al., "Tamper-Respondent Assemblies with Trace Regions of Increased Susceptibility to Breaking", U.S. Appl. No. 15/341,108, filed Nov. 2, 2016 (56 pages).
Brodsky et al., "Enclosure with Inner Tamper-Respondent Sensor(s)", U.S. Appl. No. 15/409,851, filed Jan. 19, 2017 (115 pages).
Brodsky et al., "Tamper-Respondent Assemblies with Enclosure-to-Board Protection", U.S. Appl. No. 15/423,833, filed Feb. 3, 2017 (54 pages).

* cited by examiner

TAMPER-RESPONDENT ASSEMBLY WITH NONLINEARITY MONITORING

BACKGROUND

Many activities require secure electronic communications. To facilitate secure electronic communications, an encryption/decryption system may be implemented on an electronic assembly or printed circuit board assembly that is included in equipment connected to a communications network. Such an electronic assembly is an enticing target for malefactors since it may contain codes or keys to decrypt intercepted messages, or to encode fraudulent messages. To prevent this, an electronic assembly may be mounted in an enclosure, which is then wrapped in a security sensor and encapsulated with polyurethane resin. A security sensor may be, in one or more embodiments, a web or sheet of insulating material with circuit elements, such as closely-spaced, conductive lines fabricated on it. The circuit elements are disrupted if the sensor is torn, and the tear can be sensed in order to generate an alarm signal. The alarm signal may be conveyed to a monitor circuit in order to reveal an attack on the integrity of the assembly. The alarm signal may also trigger an erasure of encryption/decryption keys stored within the electronic assembly.

SUMMARY

Provided herein, in one or more aspects, is a tamper-respondent assembly which includes: at least one tamper-respondent sensor including conductive lines forming, at least in part, at least one tamper-detect network of the at least one tamper-respondent sensor; and a detector to monitor the at least one tamper-respondent sensor, the detector applying an electrical signal to the conductive lines of the at least one tamper-respondent sensor to monitor for a non-linear conductivity change indicative of a tamper event at the at least one tamper-respondent sensor.

In one or more other aspects, a tamper-respondent assembly is provided which includes: at least one electronic component; an enclosure surrounding, at least in part, the at least one electronic component; a tamper-respondent sensor associated with the enclosure and facilitating forming a secure volume about the at least one electronic component, the tamper-respondent sensor including conductive lines forming, at least in part, a tamper-detect network of the tamper-respondent sensor; and a detector to monitor the tamper-respondent sensor, the detector applying an electrical signal to the conductive lines of the tamper-respondent sensor to monitor for a non-linear conductivity change indicative of a tamper event at the tamper-respondent sensor.

In one or more further aspects, a fabrication method is provided which includes fabricating a tamper-respondent assembly. The fabricating of the tamper-respondent assembly includes: providing at least one tamper-respondent sensor including conductive lines forming, at least in part, at least one tamper-detect network of the at least one tamper-respondent sensor; and providing a detector to monitor the at least one tamper-respondent sensor, the detector applying an electrical signal to the conductive lines of the at least one tamper-respondent sensor to monitor for a non-linear conductivity change indicative of the tamper event at the at least one tamper-respondent sensor.

Additional features and advantages are realized through the techniques of the present invention. Other embodiments and aspects of the invention are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Aspects of the present invention and certain features, advantages, and details thereof, are explained more fully below with reference to the non-limiting example(s) illustrated in the accompanying drawings. Descriptions of well-known materials, fabrication tools, processing techniques, etc., are omitted so as not to unnecessarily obscure the invention in detail. It should be understood, however, that the detailed description and the specific example(s), while indicating aspects of the invention, are given by way of illustration only, and are not by way of limitation. Various substitutions, modifications, additions, and/or arrangements, within the spirit and/or scope of the underlying inventive concepts will be apparent to those skilled in the art for this disclosure. Note further that reference is made below to the drawings, which are not drawn to scale for ease of understanding, wherein the same reference numbers used throughout different figures designate the same or similar components. Also, note that numerous inventive aspects and features are disclosed herein, and unless otherwise inconsistent, each disclosed aspect or feature is combinable with any other disclosed aspect or feature as desired for a particular application, for instance, for establishing a cooled, secure volume about an electronic component(s) or electronic assembly to be protected.

Figure 1:
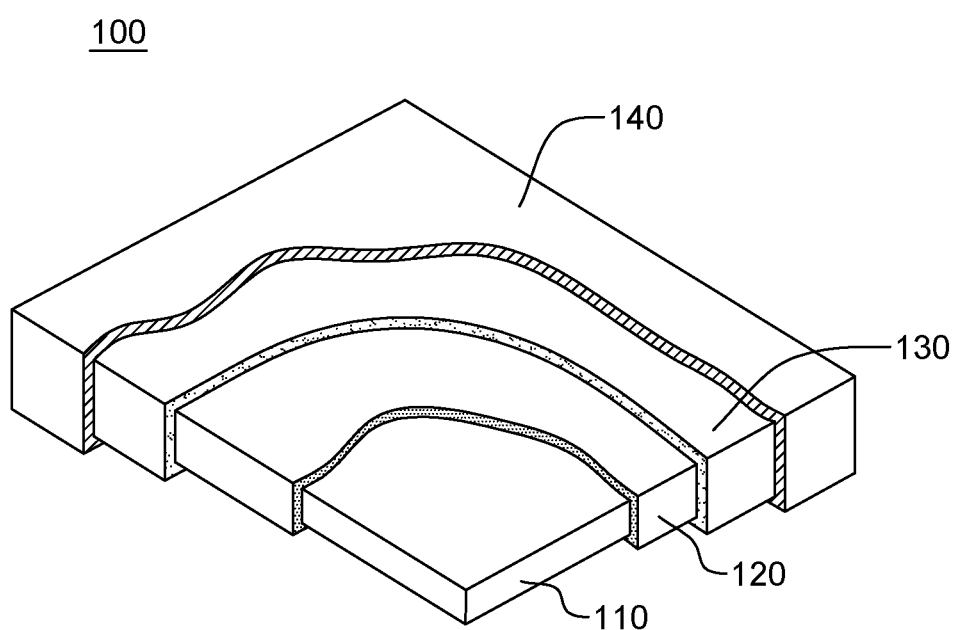
FIG. 1 is a partial cut-away of one embodiment of a tamper-proof electronic package.

Reference is first made to FIG. 1, which illustrates one approach for an electronic package 100 configured as a tamper-proof electronic package for purposes of discussion. In the depicted embodiment, an electronic assembly enclosure 110 is provided containing, for instance, an electronic assembly, which in one embodiment may include a plurality of electronic components, such as an encryption and/or decryption module and associated memory. The encryption and/or decryption module may comprise security-sensitive information with, for instance, access to the information stored in the module requiring use of a variable key, and with the nature of the key being stored in the associated memory within the enclosure.

In one or more implementations, a tamper-proof electronic package or tamper-respondent assembly, such as depicted, is configured or arranged to detect attempts to tamper-with or penetrate into electronic assembly enclosure 110. Accordingly, electronic assembly enclosure 110 also includes, for instance, a monitor circuit which, if tampering is detected, activates an erase circuit to erase information stored within the associated memory, as well as the encryption and/or decryption module within the communications card. These components may be mounted on, and interconnected by, a multilayer circuit board, such as a printed circuit board or other multilayer substrate, and be internally or externally powered via a power supply provided within the electronic assembly enclosure.

In the embodiment illustrated, and as one example only, electronic assembly enclosure 110 may be surrounded by a tamper-respondent sensor 120, an encapsulant 130, and an outer, thermally conductive enclosure 140. In one or more implementations, tamper-respondent sensor 120 may include a tamper-respondent laminate that is folded around electronic assembly enclosure 110, and encapsulant 130 may be provided in the form of a molding. Tamper-respondent sensor 120 may include various detection layers, which are monitored through, for instance, a ribbon cable by the enclosure monitor, against attempts to penetrate enclosure 110 and damage the enclosure monitor or erase circuit, before information can be erased from the encryption module. The tamper-respondent sensor may be, for example, any such article commercially available or described in various publications and issued patents, or any enhanced article such as disclosed herein.

By way of example, tamper-respondent sensor 120 may be formed as a tamper-respondent laminate comprising a number of separate layers with, for instance, an outermost lamination-respondent layer including a matrix of, for example, diagonally-extending or sinusoidally-extending, conductive or semi-conductive lines printed onto a regular, thin insulating film. The matrix of lines forms a number of continuous conductors which would be broken if attempts are made to penetrate the film. The lines may be formed, for instance, by printing conductive traces onto the film and selectively connecting the lines on each side, by conductive vias, near the edges of the film. Connections between the lines and an enclosure monitor of the communications card may be provided via, for instance, one or more ribbon cables. The ribbon cable itself may be formed of lines of conductive material printed onto an extension of the film, if desired. Connections between the matrix and the ribbon cable may be made via connectors formed on one edge of the film. As noted, the laminate may be wrapped around the electronic assembly enclosure to define the tamper-respondent sensor 120 surrounding enclosure 110.

In one or more implementations, the various elements of the laminate may be adhered together and wrapped around enclosure 110, in a similar manner to gift-wrapping a parcel, to define the tamper-respondent sensor shape 120. The assembly may be placed in a mold which is then filled with, for instance, cold-pour polyurethane, and the polyurethane may be cured and hardened to form an encapsulant 130. The encapsulant may, in one or more embodiments, completely surround the tamper-respondent sensor 120 and enclosure 110, and thus form a complete environmental seal, protecting the interior of the enclosure. The hardened polyurethane is resilient and increases robustness of the electronic package in normal use. Outer, thermally conductive enclosure 140 may optionally be provided over encapsulant 130 to, for instance, provide further structural rigidity to the electronic package.

When considering tamper-proof packaging, the electronic package needs to maintain defined tamper-proof requirements, such as those set forth in the National Institutes of Standards and Technology (NIST) Publication FIPS 140-2, which is a U.S. Government Computer Security Standard, used to accredit cryptographic modules. The NIST FIPS 140-2 defines four levels of security, named Level 1 to Level 4, with Security Level 1 providing the lowest level of security, and Security Level 4 providing the highest level of security. At Security Level 4, physical security mechanisms are provided to establish a complete envelope of protection around the cryptographic module, with the intent of detecting and responding to any unauthorized attempt at physical access. Penetration of the cryptographic module enclosure from any direction has a very high probability of being detected, resulting in the immediate zeroization of all plain text critical security parameters (CSPs). Security Level 4 cryptographic modules are useful for operation in physically unprotected environments. Security Level 4 also protects a cryptographic module against a security compromise due to environmental conditions or fluctuations outside the module's normal operating ranges for voltage and temperature. Intentional excursions beyond the normal operating ranges may be used by an attacker to thwart the cryptographic module's defenses. The cryptographic module is required to either include specialized environmental protection features designed to detect fluctuations and zeroize, critical security parameters, or to undergo rigorous environmental failure testing to provide reasonable assurances that the module will not be affected by fluctuations outside the normal operating range in a manner than can compromise the security of the module.

To address the demands for ever-improving anti-intrusion technology, and the higher-performance encryption/decryption functions being provided, enhancements to the tamper-proof, tamper-evident packaging for the electronic component(s) or assembly at issue are desired.

Numerous enhancements are described herein to, for instance, tamper-proof electronic packages or tamper-respondent assemblies. The numerous inventive aspects described herein may be used singly, or in any desired combination. Additionally, in one or more implementations, the enhancements described herein may be provided to work within defined space limitations for existing packages.

Disclosed hereinbelow with reference to FIGS. 2-11 are various approaches and/or enhancements to creating, for instance, a secure volume for accommodating one or more electronic components, such as one or more encryption and/or decryption modules and associated components of, for instance, a communications card or other electronic assembly to be protected.

Figure 2:
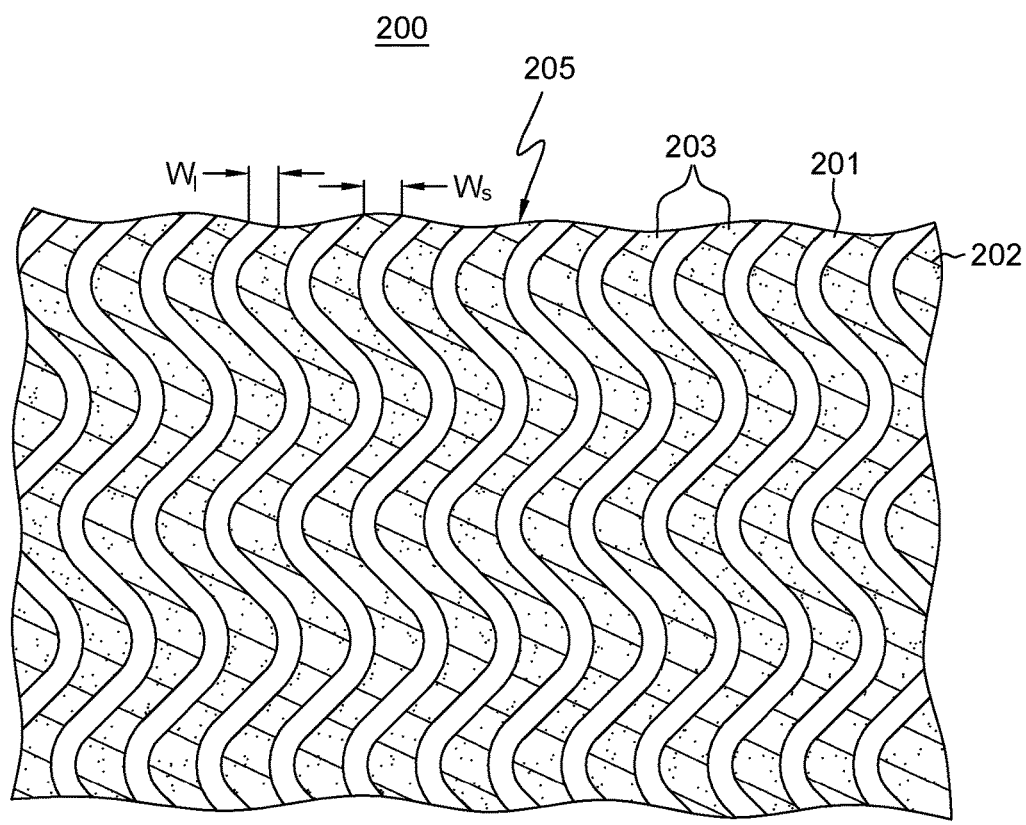
FIG. 2 depicts one embodiment of a tamper-respondent sensor with conductive lines forming, at least in part, at least one tamper-detect network, in accordance with one or more aspects of the present invention.

FIG. 2 depicts a portion of one embodiment of a tamper-respondent layer 205 (or laser and pierce-respondent layer) of a tamper-respondent sensor 200 or security sensor, such as discussed herein. In FIG. 2, tamper-respondent layer 205 includes circuit lines or traces 201 provided on one or both opposite sides of a flexible layer 202, which in one or more embodiments, may be a flexible insulating layer or film. FIG. 2 illustrates circuit lines 201 on, for instance, one side of flexible layer 202, with the traces on the opposite side of the film being, for instance, the same pattern, but (in one or more embodiments) offset to lie directly below spaces 203, between circuit lines 201. As described below, the circuit lines on one side of the flexible layer may be of a line width $W_l$ and have a pitch or line-to-line spacing $W_s$ such that piercing of the layer 205 at any point results in damage to at least one of the circuit lines traces 201. In one or more implementations, the circuit lines may be electrically connected in-series or parallel to define one or more conductors which may be electrically connected in a network to an enclosure monitor, which may, in one or more implementations, monitor the resistance of the lines. Detection of an increase, or other change, in resistance, caused by cutting or damaging one of the traces, will cause information within the encryption and/or decryption module to be erased. Providing conductive lines 201 in a pattern, such as a sinusoidal pattern, may advantageously make it more difficult to breach tamper-respondent layer 205 without detection. Note, in this regard, that conductive lines 201 could be provided in any desired pattern. For instance, in an alternate implementation, conductive lines 201 could be provided as parallel, straight conductive lines, if desired, and the pattern or orientation of the pattern may vary between sides of a layer, and/or between layers.

As noted, as intrusion technology continues to evolve, anti-intrusion technology needs to continue to improve to stay ahead. In one or more implementations, the above-summarized tamper-respondent sensor 200 of FIG. 2 may be disposed over an outer surface of an electronic enclosure, such as an electronic enclosure described above in connection with FIG. 1. Alternatively, as described further herein, the tamper-respondent sensor may cover or line an inner surface of an electronic enclosure to provide a secure volume about at least one electronic component to be protected. Still further, the tamper-respondent sensor, or more particularly, the tamper-detect circuit(s) of the sensor, could be embedded within a multilayer circuit board described below.

In one or more aspects, disclosed herein is a tamper-respondent sensor 200 with circuit lines 201 having reduced line widths $W_l$ of, for instance, 200 μm, or less, such as less than or equal to 100 μm, or even more particularly, in the range of 30-70 μm. This is contrasted with conventional trace widths, which are typically on the order of 250 μm or larger. Commensurate with reducing the circuit line width WI, line-to-line spacing width $W_s$ 203 is also reduced to less than or equal to 200 μm, such as less than or equal to 100 μm, or for instance, in a range of 30-70 μm. Advantageously, by reducing the line width $W_l$ and line-to-line spacing $W_s$ of circuit lines 201 within tamper-respondent sensor 200, the circuit line width and pitch is on the same order of magnitude as the smallest intrusion instruments currently available, and therefore, any intrusion attempt will necessarily remove a sufficient amount of a circuit line(s) to cause resistance to change, and thereby the tamper intrusion to be detected. Note that, by making the circuit line width of the smaller dimensions disclosed herein, any cutting or damage to the smaller-dimensioned circuit line will also be more likely to be detected, that is, due to a greater change in resistance. For instance, if an intrusion attempt cuts a 100 μm width line, it is more likely to reduce the line width sufficiently to detect the intrusion by a change in resistance. A change in a narrower line width is more likely to result in a detectable change in resistance, compared with, for instance, a 50% reduction in a more conventional line width of 350 μm to, for instance, 175 The smaller the conductive circuit line width becomes, the more likely that a tampering of that line will be detected.

Note also that a variety of materials may advantageously be employed to form the circuit lines when implemented using resistance monitoring. For instance, the circuit lines may be formed of a conductive ink (such as a carbon-loaded conductive ink) printed onto one or both opposite sides of one or more of the flexible layers 202 in a stack of such layers. Alternatively, a metal or metal alloy could be used to form the circuit lines, such as copper, silver, intrinsically conductive polymers, carbon ink, or nickel-phosphorus (NiP), or Omega-Ply®, offered by Omega Technologies, Inc. of Culver City, Calif. (USA), or Ticer™ offered by Ticer Technologies, Chandler, Ariz. (USA). Note that the process employed to form the fine circuit lines or traces on the order described herein is dependent, in part, on the choice of material used for the circuit lines. For instance, if copper circuit lines are being fabricated, then additive processing, such as plating up copper traces, or subtractive processing, such as etching away unwanted copper between trace lines, may be employed. By way of further example, if conductive ink is employed as the circuit line material, fine circuit lines on the order disclosed herein can be achieved by focusing on the rheological properties of the conductive ink formulation. Further, rather than simple pneumatics of pushing conductive ink through an aperture in a stencil with a squeegee, the screen emulsion may be characterized as very thin (for instance, 150 to 200 μm), and a squeegee angle may be used such that the ink is sheared to achieve conductive ink breakaway rather than pumping the conductive ink through the screen apertures. Note that the screen for fine line width printing such as described herein may have the following characteristics in one specific embodiment: a fine polyester thread for both warp and weave on the order of 75 micrometers; a thread count between 250-320 threads per inch; a mesh thickness of, for instance, 150 micrometers; an open area between threads that is at least 1.5× to 2.0× the conductive ink particle size; and to maintain dimensional stability of the print, the screen snap-off is kept to a minimum due the screen strain during squeegee passage.

In a further aspect, the flexible layer 202 itself may be further reduced in thickness from a typical polyester layer by selecting a crystalline polymer to form the flexible layer or substrate. By way of example, the crystalline polymer could comprise polyvinylidene difluoride (PVDF), or Kapton, or other crystalline polymer material. Advantageously, use of a crystalline polymer as the substrate film may reduce thickness of the flexible layer 202 to, for instance, 2 mils thick from a more conventional amorphous polyester layer of, for instance, 5-6 mils. A crystalline polymer can be made much thinner, while still maintaining structural integrity of the flexible substrate, which advantageously allows for far more folding, and greater reliability of the sensor after folding. Note that the radius of any fold or curvature of the sensor is necessarily constrained by the thickness of the layers comprising the sensor. Thus, by reducing the flexible layer thickness to, for instance, 2 mils, then in a four tamper-respondent layer stack, the stack thickness can be reduced from, for instance, 20 mils in the case of a typical polyester film, to 10 mils or less with the use of crystalline polymer films.

Figure 3A:
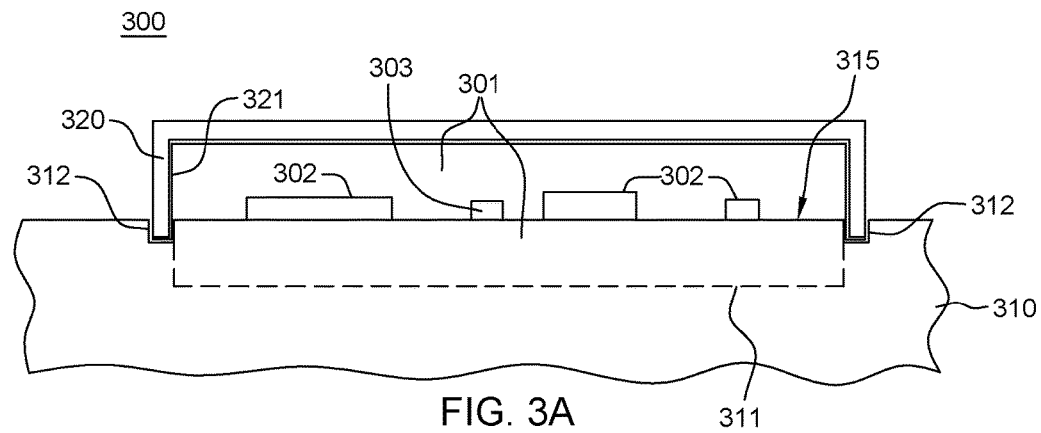
FIG. 3A is a cross-sectional elevational view of another embodiment of a tamper-proof electronic package, or tamper-respondent assembly, which includes (in part) an enclosure, and a multilayer circuit board with an embedded tamper-respondent sensor, in accordance with one or more aspects of the present invention.
Figure 3B:
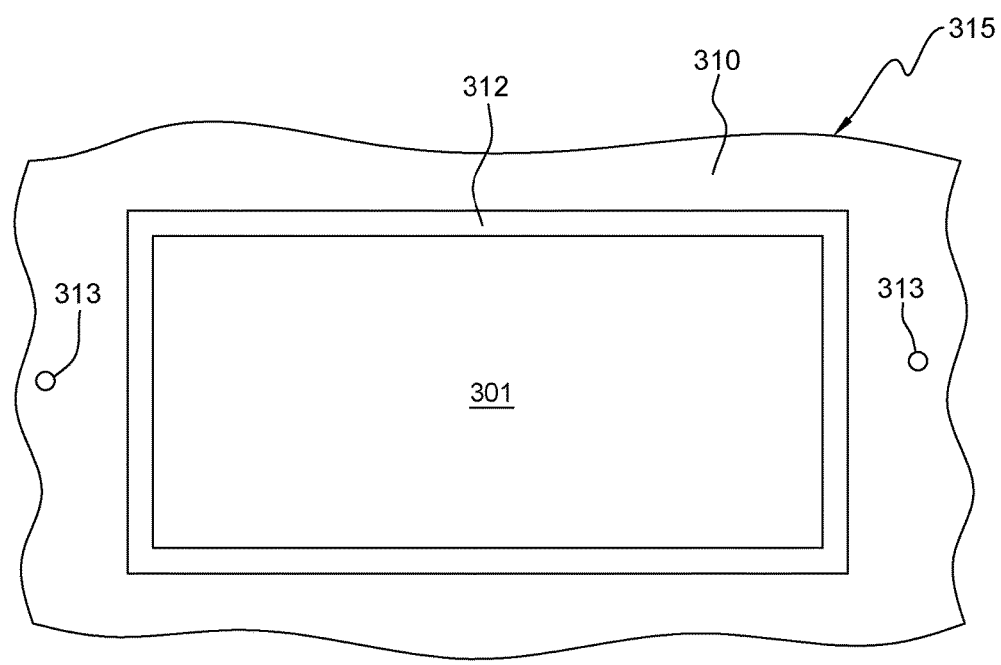
FIG. 3B is a top plan view of the multilayer circuit board of FIG. 3A, depicting one embodiment of the secure volume defined, in part, within the multilayer circuit board, in accordance with one or more aspects of the present invention.

FIGS. 3A & 3B depict one embodiment of a tamper-proof electronic package 300, or tamper-respondent assembly, which comprises one or more electronic components, such as a circuit 315 and/or electronic devices (or elements) 302 to be protected, in accordance with one or more further aspects of the present invention.

Referring collectively to FIGS. 3A & 3B, circuit 315 resides on or is embedded within a multilayer circuit board 310, which also has an embedded tamper-respondent sensor 311 that facilitates defining, in part, a secure volume 301 associated with multilayer circuit board 310 that (in one or more embodiments) extends into multilayer circuit board 310. In particular, in the embodiment of FIGS. 3A & 3B, secure volume 301 may exist partially within multilayer circuit board 310, and partially above multilayer circuit board 310. One or more electronic devices 302 are mounted to multilayer circuit board 310 within secure volume 301 and may comprise, for instance, one or more encryption modules and/or decryption modules, and/or associated components, to be protected within the tamper-proof electronic package. In one or more implementations, the one or more electronic components to be protected may comprise, for instance, a secure communications card of a computer system.

Tamper-proof electronic package 300 further includes an enclosure 320, such as a pedestal-type enclosure, mounted to multilayer circuit board 310 within, for instance, a continuous groove (or trench) 312 formed within an upper surface of multilayer circuit board 310, and secured to the multilayer circuit board 310 via, for instance, a structural adhesive disposed within continuous groove 312. In one or more embodiments, enclosure 320 may comprise a thermally conductive material and operate as a heat sink for facilitating cooling of the one or more electronic components 302 within the secure volume. A security mesh or tamper-respondent sensor 321 may be associated with enclosure 320, for example, wrapping around the inner surface of enclosure 320, to facilitate defining, in combination with tamper-respondent sensor 311 embedded within multilayer circuit board 310, secure volume 301. In one or more implementations, tamper-respondent sensor 321 may extend down into continuous groove 312 in multilayer circuit board 310 and may, for instance, even wrap partially or fully around the lower edge of enclosure 320 within continuous groove 312 to provide enhanced tamper detection where enclosure 320 couples to multilayer circuit board 310. In one or more implementations, enclosure 320 may be securely affixed to multilayer circuit board 310 using, for instance, a bonding material such as an epoxy or other adhesive.

Briefly described, tamper-respondent sensor 321 may comprise, in one or more examples, one or more tamper-respondent layers which include circuit lines or traces provided on one or both sides of a flexible layer, which in one or more implementations, may be a flexible insulating layer or film. The circuit lines on one or both sides of the flexible layer may be of a line width and have a pitch or line-to-line spacing such that piercing of the layer at any point results in damage to one or more of the circuit lines or traces. In one or more implementations, the circuit lines may define one or more conductors which may be electrically connected in a network to an enclosure monitor or detector 303, which monitors, for instance, resistance on the lines, or as described below, in the case of conductors, may monitor for a nonlinearity, or non-linear conductivity change, on the conductive lines. Detection of a change in resistance or a nonlinearity caused by cutting or damaging one or more of the lines, will cause information within the secure volume to be automatically erased. The conductive lines of the tamper-respondent sensor may be in any desired pattern, such as a sinusoidal pattern, to make it more difficult to breach the tamper-respondent layer without detection.

For resistive monitoring, a variety of materials may be employed to form the circuit lines. For instance, the circuit lines may be formed of a metal or metal alloy could be used to form the circuit lines, such as copper, silver, intrinsically-conductive polymers, carbon ink, or nickel phosphorous (NiP), or Omega-ply®, offered by Omega Technologies, Inc., of Culver City, Calif. (USA), or Ticer™, offered by Ticer Technologies, Chandler, Ariz. (USA). For nonlinearity monitoring, which as noted is described below, the circuit lines could be formed of a metal, such as copper, silver, aluminum, etc., or a metal alloy. The process employed to form the fine circuit lines or traces is dependent, in part, on the choice of materials used for the circuit lines. For instance, if copper circuit lines are fabricated, then additive processing, such as plating of copper traces, or subtractive processing, such as etching away unwanted copper between trace lines, may be employed.

As noted, in one or more implementations, the circuit lines of the tamper-respondent sensor(s) lining the inner surface(s) of enclosure 320, or even printed directly onto one or more layers formed over the inner surface of enclosure 320, may be connected to define one or more detect networks.

If a flexible layer is used over the inner surface of enclosure 320, then the flexible layer may be formed of a crystalline polymer material. For instance, the crystalline polymer could comprise polyvinylidene difluoride (PVDF), or Kapton, or other crystalline polymer material. Advantageously, a crystalline polymer may be made much thinner, while still maintaining structural integrity of the flexible substrate, which also allows for enhanced folding, and greater reliability of the sensor after folding.

As depicted in FIG. 3B, one or more external circuit connection vias 313 may be provided within multilayer circuit board 310 for electrically connecting to the one or more electronic components within secure volume 301. These one or more external circuit connection vias 313 may electrically connect to one or more external signal lines or planes (not shown) embedded within multilayer circuit board 310 and extending, for instance, into a secure base region of (or below) secure volume 301, as explained further below. Electrical connections to and from secure volume 301 may be provided by coupling to such external signal lines or planes within the multilayer circuit board 310.

As noted, secure volume 301 may be sized to house one or more electronic components to be protected, and may be constructed to extend into multilayer circuit board 310. In one or more implementations, multilayer circuit board 10 includes electrical interconnect within the secure volume 301 defined in the board, for instance, for electrically connecting one or more tamper-respondent layers of the embedded tamper-respondent sensor 311 to associated monitor circuitry also disposed within secure volume 301, along with, for instance, one or more daughter cards, such as memory DIMMs, PCIe cards, processor cards, etc.

Note that the packaging embodiment depicted in FIGS. 3A & 3B is presented by way of example only. Other configurations of enclosure 320, or multilayer circuit board 310 may be employed, and/or other approaches to coupling enclosure 320 and multilayer circuit board 310 may be used. For instance, in one or more alternate implementations, enclosure 320 may be securely affixed to an upper surface of multilayer circuit board 310 (without a continuous groove) using, for instance, a structural bonding material such as an epoxy or other adhesive.

Figure 4:
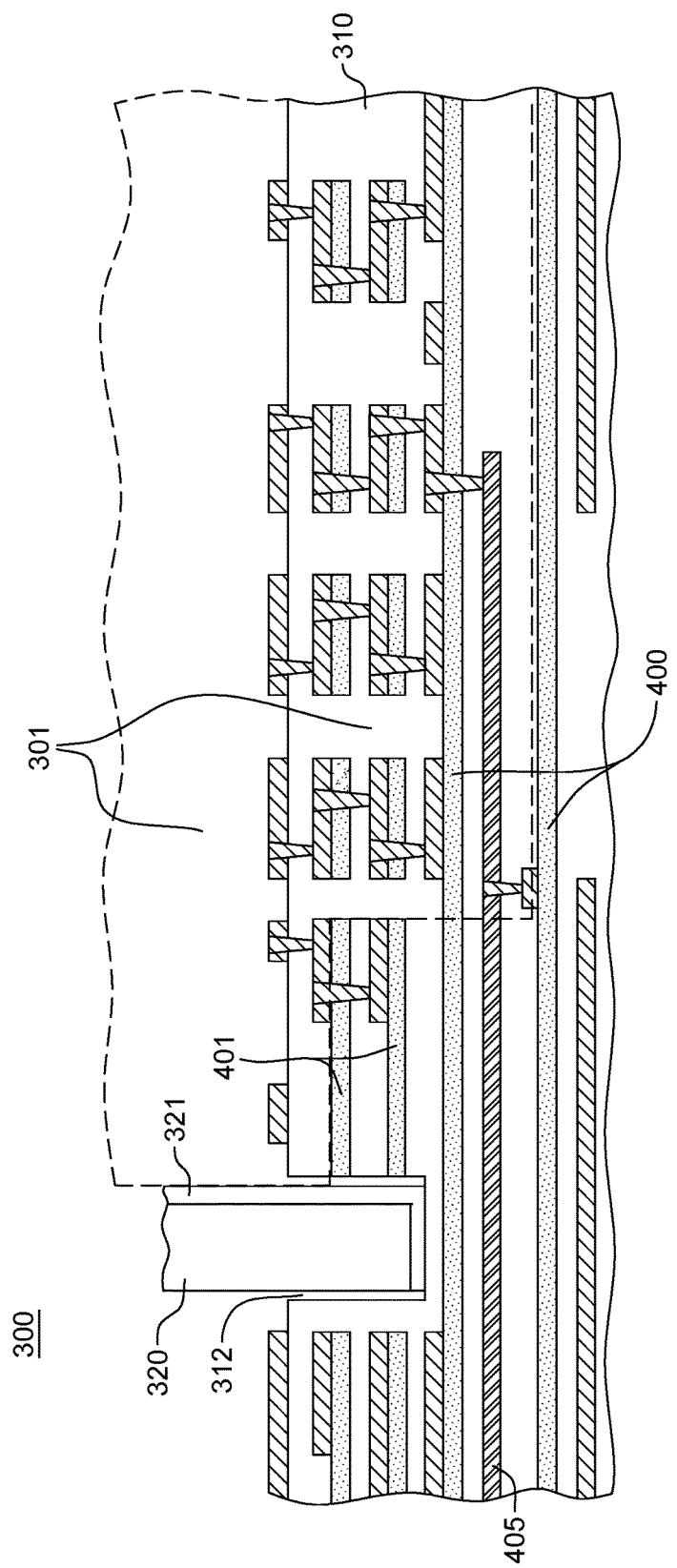
FIG. 4 is a partial cross-sectional elevational view of a more detailed embodiment of the tamper-respondent assembly of FIGS. 3A & 3B comprising (in part) an enclosure, and a multilayer circuit board with embedded tamper-respondent sensor, in accordance with one or more aspects of the present invention.

By way of further example, FIG. 4 depicts a partial cross-sectional elevational view of a more detailed embodiment of tamper-proof electronic package 300, and in particular, of multilayer circuit board 310, to which enclosure 320 is secured. In this configuration, the embedded tamper-respondent sensor includes multiple tamper-respondent layers including, by way of example, at least one tamper-respondent mat (or base) layer 400, and at least one tamper-respondent frame 401. In the example depicted, two tamper-respondent mat layers 400 and two tamper-respondent frames 401 are illustrated, by way of example only. The lower-most tamper-respondent mat layer 400 may be a continuous sense or detect layer extending completely below the secure volume being defined within and/or above multilayer circuit board 310. One or both tamper-respondent mat layers 400 below secure volume 301 may be partitioned into multiple circuit zones. Within each tamper-respondent mat layer, or more particularly, within each circuit zone of each tamper-respondent mat layer, multiple circuits or conductive traces may be provided in any desired configuration. Further, the conductive traces within the tamper-respondent layers may be implemented as, for instance, a resistive layer.

As illustrated, one or more external signal lines or planes 405 may enter secure volume 301 between, in one embodiment, two tamper-respondent mat layers 400, and then electrically connect upwards into the secure volume 301 through one or more conductive vias, arranged in any desired location and pattern. In the configuration depicted, the one or more tamper-respondent frames 401 are disposed at least inside of the area defined by continuous groove 312 accommodating the base of enclosure 320. Together with the tamper-respondent sensor(s) 321 associated with enclosure 320, tamper-respondent frames 301, and tamper-respondent mat layers 400, define secure volume 301, which may extend, in part, into multilayer circuit board 310. With secure volume 301 defined, in part, within multilayer circuit board 310, the external signal line(s) 405 may be securely electrically connected to, for instance, the one or more electronic components mounted to, or of, multilayer circuit board 310 within secure volume 301. In addition, secure volume 301 may accommodate electrical interconnection of the conductive traces of the multiple tamper-respondent layers 400, 301, for instance, via appropriate monitor circuitry.

Added security may be provided by extending tamper-respondent mat layers 400 (and if desired, tamper-respondent frames 401) outward past the periphery of enclosure 320. In this manner, a line of attack may be made more difficult at the interface between enclosure 320 and multilayer circuit board 310 since the attack would need to clear, for instance, tamper-respondent mat layers 400, the enclosure 320, as well as the tamper-respondent frames 401 of the embedded tamper-respondent sensor.

Numerous variations on multilayer circuit board 310 of FIGS. 3A-4 are possible. For instance, in one embodiment, the embedded tamper-respondent sensor may include one or more tamper-respondent mat layers 400 and one or more tamper-respondent frames 401, such as described above, and a tri-plate structure comprising one or more external signal lines or layers sandwiched between an upper ground plane and a lower ground plane. In this configuration, high-speed transfer of signals to and from the secure volume, and in particular, to and from the one or more electronic components resident within the secure volume, would be facilitated.

Note also that, once within the secure volume is defined in part within multilayer circuit board 310, conductive vias within the secure volume between layers of multilayer circuit board 310 may be either aligned, or offset, as desired, dependent upon the implementation. Alignment of conductive vias may facilitate, for instance, providing a shortest connection path, while offsetting conductive vias between layers may further enhance security of the tamper-proof electronic package by making an attack into the secure volume through or around one or more tamper-respondent layers of the multiple tamper-respondent layers more difficult.

The tamper-respondent layers of the embedded tamper-respondent sensor formed within the multilayer circuit board of the electronic circuit or electronic package may include multiple conductive traces or lines formed between, for instance, respective sets of input and output contacts or vias at the trace termination points. Any pattern and any number of conductive traces or circuits may be employed in defining a tamper-respondent layer or a tamper-respondent circuit zone within a tamper-respondent layer. For instance, 4, 6, 8, etc., conductive traces may be formed in parallel (or otherwise) within a given tamper-respondent layer or circuit zone between the respective sets of input and output contacts to those conductive traces.

Figure 5:
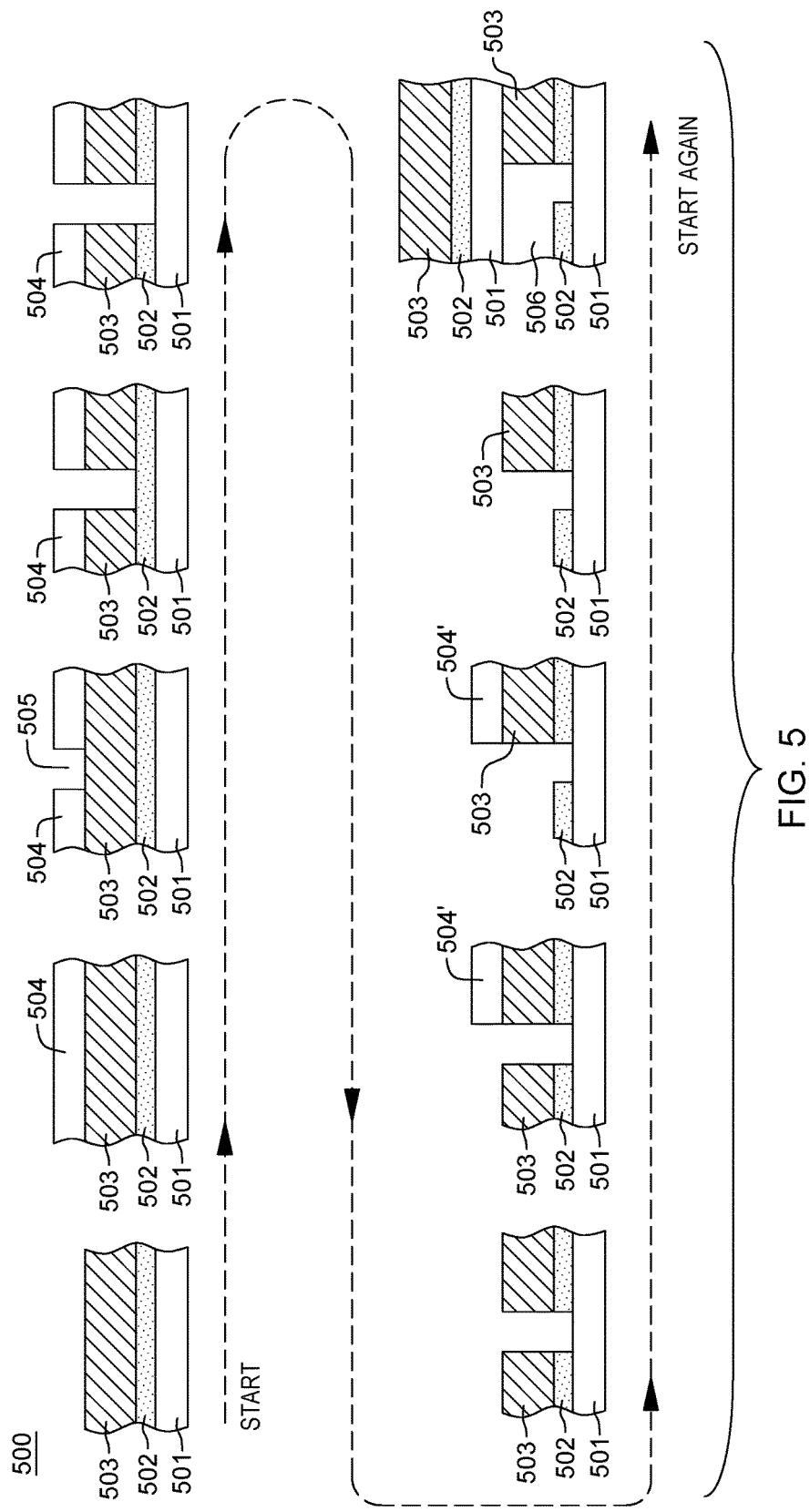
FIG. 5 depicts one embodiment of a process of fabricating a multilayer circuit board with an embedded tamper-respondent sensor, in accordance with one or more aspects of the present invention.

In one or more implementations, the multilayer circuit board may be a multilayer wiring board or printed circuit board formed, for instance, by building up the multiple layers of the board. FIG. 5 illustrates one embodiment for forming and patterning a tamper-respondent layer within such a multilayer circuit board.

As illustrated in FIG. 5, in one or more implementations, a tamper-respondent layer, such as a tamper-respondent mat layer or a tamper-respondent frame disclosed herein, may be formed by providing a material stack comprising, at least in part, a structural layer 501, such as a pre-preg (or preimpregnated) material layer, a trace material layer 502 for use in defining the desired trace patterns, and an overlying conductive material layer 503, to be patterned to define conductive contacts or vias electrically connecting to the pattern of traces being formed within the trace material layer 502, for instance, at trace terminal points. In one or more implementations, the trace material layer 502 may comprise nickel phosphorous (NiP), and the overlying conductive layer 503 may comprise copper. Note that these materials are identified by way of example only, and that other trace and/or conductive materials may be used within the build-up 500.

A first photoresist 504 is provided over build-up 500, and patterned with one or more openings 505, through which the overlying conductive layer 503 may be etched. Depending on the materials employed, and the etch processes used, a second etch process may be desired to remove portions of trace material layer 502 to define the conductive traces of the subject tamper-respondent layer. First photoresist 504 may then be removed, and a second photoresist 504' is provided over the conductive layer 503 features to remain, such as the input and output contacts. Exposed portions of conductive layer 503 are then etched, and the second photoresist 504' may be removed, with any opening in the layer being filled, for instance, with an adhesive (or pre-preg) and a next build-up layer is provided, as shown. Note that in this implementation, most of overlying conductive layer 503 is etched away, with only the conductive contacts or vias remaining where desired, for instance, at the terminal points of the traces formed within the layer by the patterning of the trace material layer 502. Note that any of a variety of materials may be employed to form the conductive lines or traces within a tamper-respondent layer. Nickel-phosphorous (NiP) is particularly advantageous as a material since it is resistant to contact by solder, or use of a conductive adhesive to bond to it, making it harder to bridge from one circuit or trace to the next during an attempt to penetrate into the protected secure volume of the electronic circuit. Other materials which could be employed include OhmegaPly®, offered by Ohmega Technologies, Inc., of Culver City, Calif. (USA), or Ticer™, offered by Ticer Technologies of Chandler, Ariz. (USA).

The trace lines or circuits within the tamper-respondent layers, and in particular, the tamper-respondent circuit zones, of the embedded tamper-respondent sensor, along with the tamper-respondent detector monitoring the enclosure, may be electrically connected to detect or compare circuitry provided, for instance, within secure volume 301 (FIG. 3A) of the tamper-proof electronic package. The detect circuitry may include various bridge or compare circuits, and conventional printed wiring board electrical interconnect inside secure volume 301 (FIG. 3A), for instance, located within the secure volume defined by the tamper-respondent frames 401 (FIG. 4), and the tamper-respondent mat layers 400 (FIG. 4).

Note that advantageously, different tamper-respondent circuit zones on different tamper-respondent layers may be electrically interconnected into, for instance, the same detect circuitry. Thus, any of a large number of interconnect configurations may be possible. For instance, if each of two tamper-respondent mat layers contains 30 tamper-respondent circuit zones, and each of two tamper-respondent frames contains 4 tamper-respondent circuit zones, then, for instance, the resultant 68 tamper-respondent circuit zones may be connected in any configuration within the secure volume to create the desired arrangement of circuit networks within the secure volume being monitored for changes in resistance or tampering. Note in this regard, that the power supply or battery for the tamper-respondent sensor may be located internal or external to the secure volume, with the sensor being configured to trip and destroy any protected or critical data if the power supply or battery is tampered with.

Figure 6:
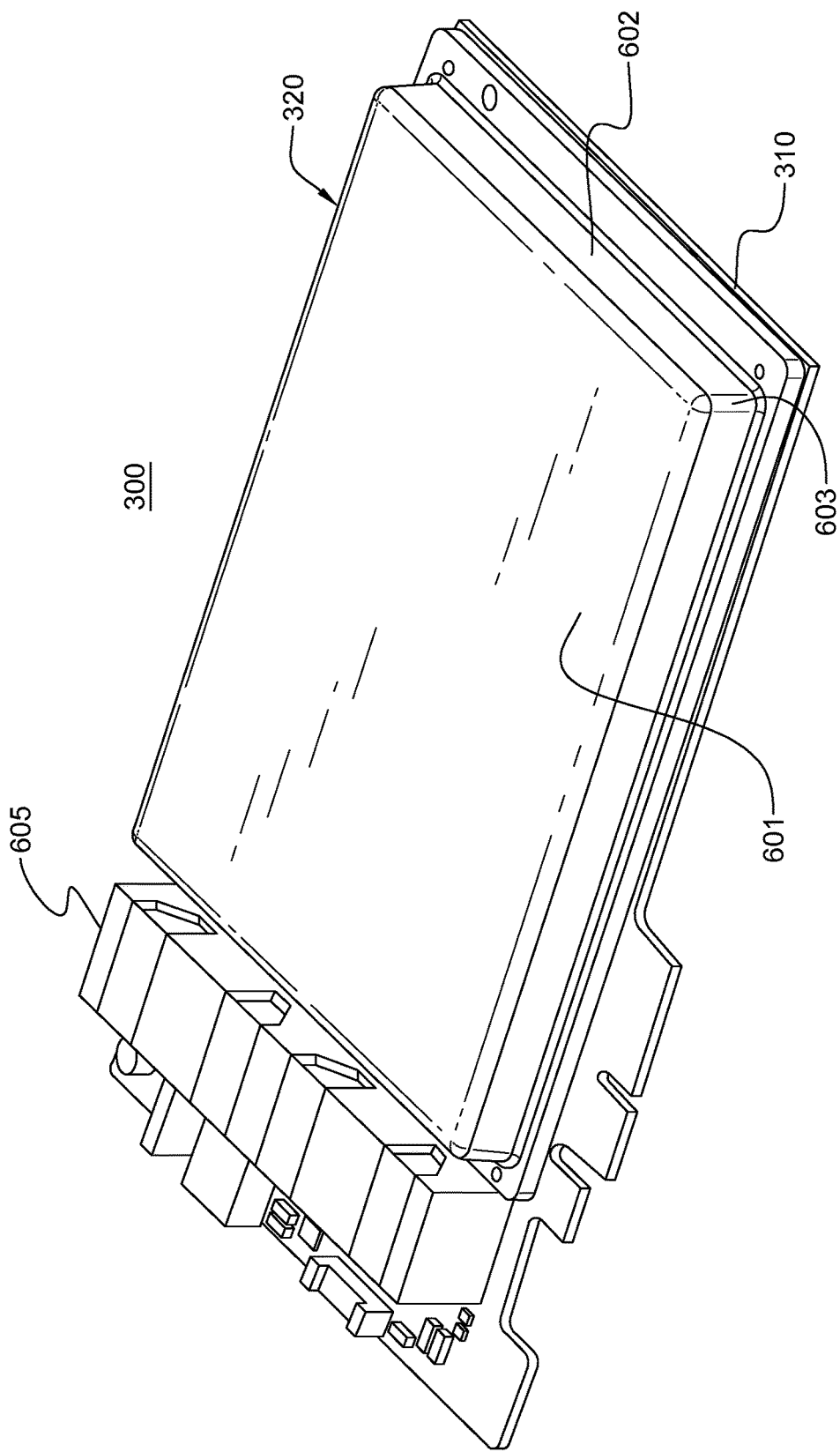
FIG. 6 is an isometric view of one embodiment of a tamper-respondent assembly, in accordance with one or more aspects of the present invention.

By way of further example, an isometric view of one embodiment of a tamper-proof electronic package 300 is depicted in FIG. 6, wherein an enclosure 320 is shown sealed to multilayer circuit board 310 to define a secure volume about one or more electronic components, as described herein. In the embodiment depicted, enclosure 320 may be formed of a thermally conductive material, and includes a main surface 601 and sidewall(s) 602 which include sidewall corners 603. An inner surface of enclosure 220 would include an inner main surface, and an inner sidewall surface corresponding to main surface 601 and sidewall(s) 602 respectively, with the inner main surface and inner sidewall surfaces being covered, at least in part, by one or more tamper-respondent sensors, such as described above. A power supply 605 or battery for the tamper-respondent sensor may be located, as depicted in this embodiment, external to the secure volume, with the tamper-respondent detector being configured to trip and destroy any protected or critical data if the power supply or battery is tampered with. Enclosure 320 may be adhered or mechanically affixed to multilayer circuit board 310, which as noted above, may include its own embedded tamper-respondent sensor(s).

By way of further enhancement, disclosed herein is tamper-detect monitoring using nonlinearity sensing within the tamper-respondent assembly. Increased tamper-respondent sensor sensitivity and robustness is advantageously provided by providing a detector which monitors the tamper-respondent sensor(s) of the assembly by applying an electrical signal to the conductive lines of the sensor and monitoring for a non-linear conductivity (NLC) change on one or more of the lines indicative of a tamper event at or impacting, the tamper-respondent sensor(s).

In many applications, tamper detection involves monitoring one or more sensor nets for a change in resistance, either by, for instance, direct measurement of resistive lines or circuits, or by applying Wheatstone bridges, or similar structures, to detect an attempted intrusion through a change in resistance. As explained herein, an improved tamper-proof package may be achieved by reducing the line width of the conductive lines in the detect network. Also, since certain metals, such as copper, have excellent conductivity, it is possible to impact a significant portion of a conductive line, such as a copper line, without detecting a change in resistance. Further, it is possible to shunt a copper line, and not detect the shunt, using a typical resistance measurement approach.

As disclosed herein, nonlinearity monitoring, or non-linear conductivity change monitoring, can advantageously be used to detect line breaks or shorts, as well as attempts to shunt a conductive line, or a nick or other damage to the line, making it far more difficult for a malefactor to intrude into the tamper-proof package. This nonlinearity monitoring may be used in place of resistive monitoring within the sensor, or in combination with resistive monitoring. For instance, a nonlinearity-monitored network may be provided on one layer, and a resistive-monitored network on another layer. This would advantageously increase complexity of the sensor, while also conserving battery power; that is, compared with a nonlinearity-monitored sensor only.

By way of explanation, nonlinearity evaluation is described, for instance, in U.S. Pat. No. 4,496,900, in the context of detecting defects in, for instance, a processor board. Applying nonlinearity detection to tamper-proof packaging, in accordance with one or more aspects of the present invention, detecting current-constricting defects, such as cracks, narrowed conductors, line breaks, intermittent opens, probe contacts, attempted shunts, etc., in conductors may be performed by examining the second harmonic voltages produced by passing a known, composite AC and DC signal through the conductive lines of the sensor. A test signal generator is provided, balanced and adjusted to provide the test signal, which is symmetrical, and thus provides little even harmonic distortion. The second harmonic voltages across the conductive lines result primarily from conductor nonlinearities, such as may occur in the presence of a tamper event. The use of the second harmonic technique advantageously provides testing capability for such nonlinearities, which may not be detectable using ordinary resistive testing techniques.

The nonlinearity detect theory of operation depends on local changes in resistance caused by Ohmic heating due to nonlinearities which, while conductive, might be expected to fail early during the normal life of a conductor. The composite, alternating current, plus direct current test signal, passes through the conductive path being tested in an unbalanced wave and, upon encountering a local constriction, causes a small volume of metal in the constriction to rapidly heat and cool in a fashion to generate second harmonic signals in close space relationship to the unbalanced wave. This temperature change produces a resistance change which varies monotonically with the temperature in response to the AC and DC current at the frequency of the resistance change. The resistance change produces time-varying voltage components at frequencies, including the fundamental frequency, second harmonic, third harmonic, fourth harmonic, and additional harmonics.

The second harmonic signal is the largest signal easily distinguished from the fundamental, and in one or more implementations, it is the second harmonic signal which may advantageously be amplified and detected as described herein.

The nonlinearity-generated signal may be several orders of magnitude smaller than very similar signals reflected from a good conductor occurring as a result of resistance heating. There is, however, a phase difference which permits the good conductor-generated signals to be filtered out, isolating the potential tamper-event-generated signal.

In general, provided herein are tamper-respondent assemblies and methods of fabrication which employ one or more tamper-respondent sensors and a detector to monitor the tamper-respondent sensor(s). The tamper-respondent sensor(s) includes conductive lines forming, at least in part, at least one tamper-detect network of the tamper-respondent sensor(s). The detector monitors the at least one tamper-respondent sensor by applying an electrical signal, or a test signal, to the conductive lines of the tamper-respondent sensor(s) to monitor for a non-linear conductivity change (or nonlinearity) indicative of a tamper event at the at least one tamper-respondent sensor.

In one or more embodiments, the detector may monitor a second harmonic of the electrical signal applied to the conductive lines to detect the nonlinearity indicative of the tamper event on the tamper-respondent sensor(s). By way of example, the electrical signal may have both known DC characteristics and known AC characteristics, as noted above, and explained further, for instance, in U.S. Pat. No. 4,496,900.

In one or more embodiments, the detector may periodically apply the electrical signal to the conductive lines. This approach may be beneficial in certain embodiments to conserve power, such as in implementations where a discrete power source is embedded within the secure volume of the tamper-respondent assembly.

In one or more embodiments, the conductive lines of the tamper-respondent sensor(s) are each formed with a line width $W_l$ which is $\leq 200$ µms, such as $\leq 100$ µms, as described above. By way of further example, the conductive lines of the tamper-respondent sensor(s) may be metal lines, such as copper, silver, aluminum, etc., lines, or metal alloy lines.

Further, the tamper-respondent sensor(s) may comprise at least one flexible layer, with the conductive lines being disposed on the flexible layer(s) to form, at least in part, the tamper-detect network(s), such as the above-described tamper-respondent sensor(s) on the inside of an enclosure.

In one or more further implementations, the tamper-respondent assembly may include a circuit board, and the tamper-respondent sensor(s) may include an embedded tamper-respondent sensor within the circuit board, with the conductive lines including conductive lines embedded within the circuit board.

Advantageously, monitoring for nonlinearity in the circuit lines of the tamper-respondent assembly makes it significantly more difficult for a malefactor to intrude into the package, since non-linear conductivity (NLC) monitoring methods can detect not only opens and shorts, but also when circuits are contacted by an attempted shunt of the circuits, or other cuts, notches, or damage to the circuit lines caused by a tamper attempt.

Figure 7:
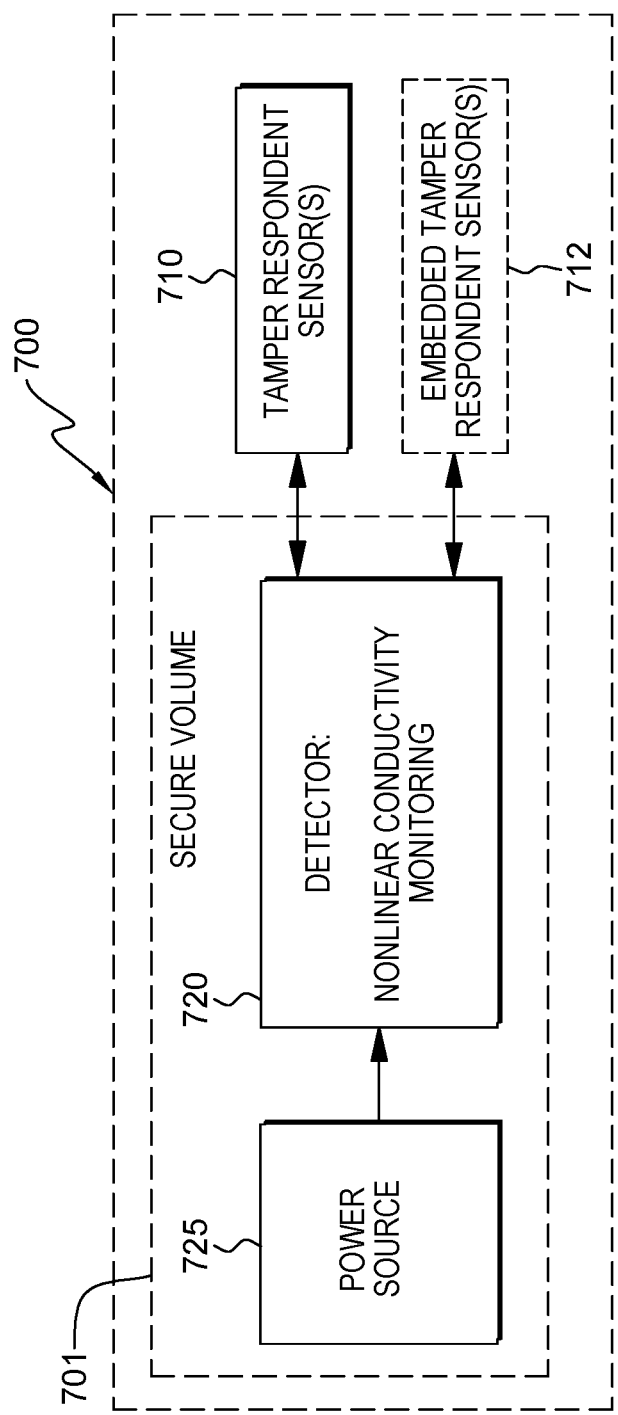
FIG. 7 is a schematic illustration of one embodiment of a tamper-respondent assembly which includes a detector for nonlinearity, or non-linear conductivity, monitoring of conductive lines of one or more tamper-respondent sensors of the tamper-respondent assembly, in accordance with one or more aspects of the present invention.

By way of example, FIG. 7 depicts one embodiment of a tamper-respondent assembly 700, which includes a secure volume 701 comprising one or more electronic components to be protected by one or more tamper-respondent sensors 710, and/or one or more embedded tamper-respondent sensors 712. Also provided within secure volume 701 is a detector which monitors for a nonlinearity or a non-linear conductivity (NLC) change due to a tamper event at one or more of the tamper-respondent sensors 710, 712. Power, in this example, may be provided by an embedded power source 725 provided within the secure volume 701 of tamper-respondent assembly 700. In one specific example, tamper-respondent assembly 700 may be a tamper-respondent assembly 300, such as described above in connection with FIGS. 3-6, which includes a secure volume 301, tamper-respondent sensor 321, as well as embedded tamper-respondent sensors 400, 401, and detector 303.

Figure 8:
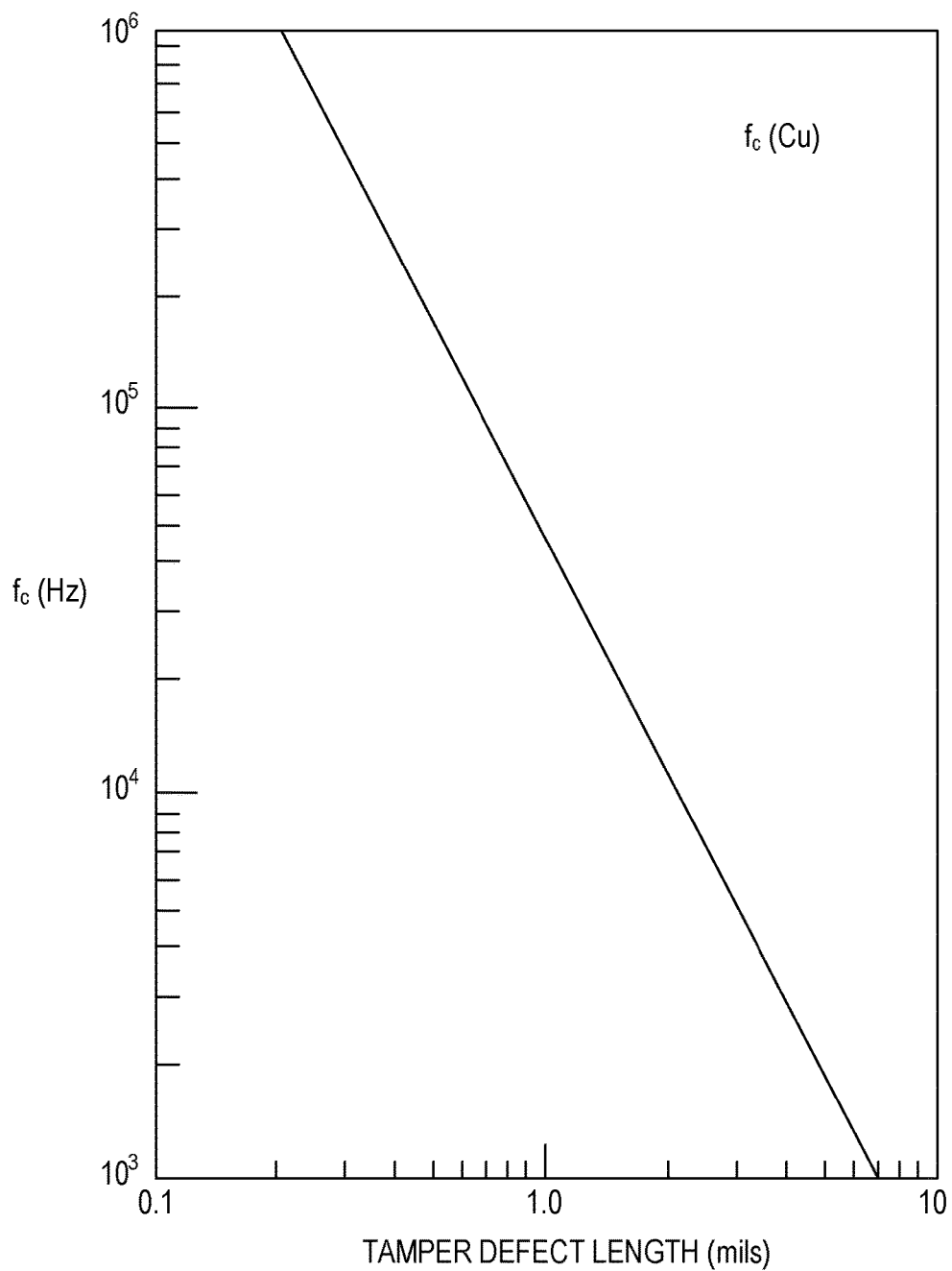
FIG. 8 depicts one example of a non-linear conductivity threshold-to-failure graph illustrating the relationship between frequency of electrical signals applied and size of a tamper event defect within a conductive line to be detected, in accordance with one or more aspects of the present invention.

FIG. 8 is a graph illustrating some of the properties of copper. The unit of the abscissa is the mil.; and the unit of the ordinate is frequency in Hertz (Hz). Cutoff frequency tends to increase as a function of decreasing length of the defect (caused, in one or more implementations, by a tamper event). Calibration may be optimized by selection of a frequency appropriate to the type (or size) of tamper event suspected.

Figure 9:
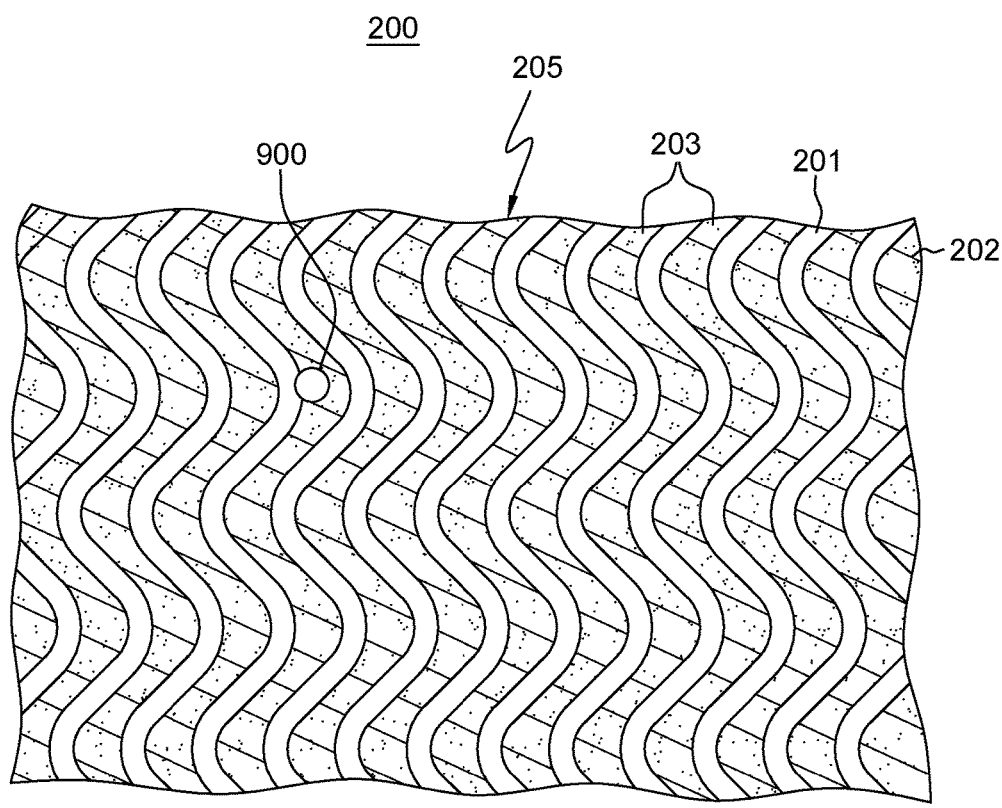
FIG. 9 depicts the tamper-respondent sensor of FIG. 2, with a tamper probe shown impacting on a conductive line of the tamper-detect network, with the intrusion being detected by a nonlinearity monitoring process, in accordance with one or more aspects of the present invention.

By way of example, FIG. 9 depicts tamper-respondent sensor 200 of FIG. 2, with a probe 900 inserted by a malefactor contacting a conductive line 201 so as to impinge or otherwise cause a restriction or defect in the conductive line that may be, for instance, a small percentage of the overall width $W_l$ of conductive line 201, such as less than 10%, or even less than 5% of the conductive line. Depending upon the sensitivity desired, the frequency $f_c$ (Hz) in the graph of FIG. 8, which refers to the test signal frequency, may be selected. As illustrated in FIG. 8, the graph depicts the frequency at which there is a 3 Db roll off, where the response is down to a factor of two. Defect length is in mils (mil=0.001"=0.0254 mm). For instance, at an expected defect length of 1.0 mil (0.0254 mm), the operator might calibrate the monitor at $10^5$ Hz, or below. To detect defects that may be 2 mils in size, the optimum frequency might be set to approximately $10^4$ Hz.

Figure 10:
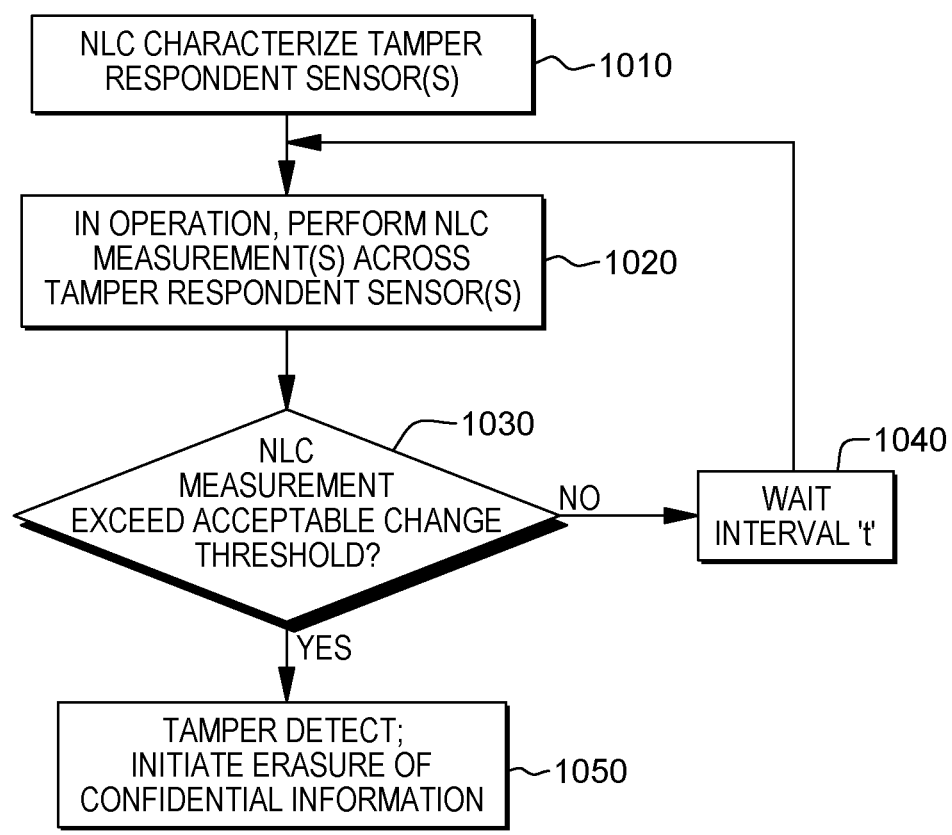
FIG. 10 depicts one embodiment of a process for nonlinearity monitoring of one or more conductive lines of a tamper-respondent sensor(s) of a tamper-respondent assembly, in accordance with one or more aspects of the present invention.

FIG. 10 illustrates one embodiment of a process 1000 for nonlinearity monitoring of one or more conductive lines of a tamper-respondent sensor in a tamper-respondent assembly. As shown, process 1000 includes initially characterizing the non-linear conductivity of the conductive lines of the tamper-respondent sensor 1010. In one or more implementations, this initial characterization may be performed prior to delivery of the tamper-respondent assembly to an end user. In operation, nonlinearity monitoring, or non-linear conductivity measurements, are obtained across the conductive lines of the tamper-respondent sensor(s) 1020. This may be achieved by using an electrical test signal comprising, for instance, both known DC characteristics and known AC characteristics such as described above, and then monitoring for a second harmonic of the applied electrical signal to detect a nonlinearity.

Processing determines whether a detected non-linear conductivity value exceeds an acceptable change characteristic 1030. For instance, the change threshold may be preset relative to the initial non-linear conductivity characterization of the conductive line(s), and be indicative of a tamper event at the tamper-respondent sensor. If the non-linear conductivity measurement does not exceed the acceptable change threshold, then processing may wait an interval of time, such as 1 sec., 5 sec., etc., before repeating the process 1040. This periodic repeating of applying the electrical test signal may be advantageous in cases where it is desirable to conserve power within the tamper-respondent assembly. If the non-linear conductivity measurement results in exceeding the acceptable change threshold, then a tamper-detect event is identified, which initiates erasure of confidential information within the secure volume 1050.

Figure 11:
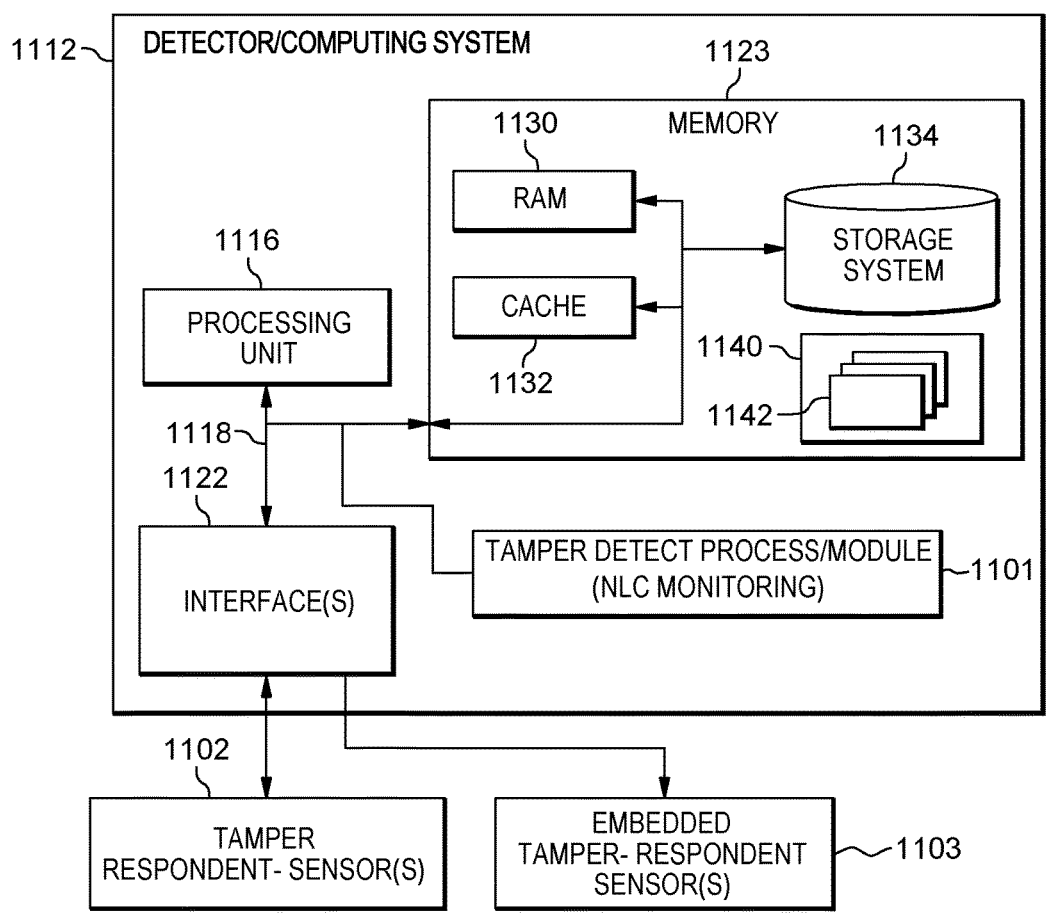
FIG. 11 depicts one embodiment of a detector or a computing system which may implement one or more of the monitoring, detecting, and/or control of a tamper-respondent assembly, in accordance with one or more aspects of the present invention.

Referring next to FIG. 11, a schematic of an example of a data processing system 1100 is shown, which may be used to implement one or more aspects of the present invention, such as the detector. Data processing system 1100 is only one example of a suitable data processing system and is not intended to suggest any limitation as to the scope of use or functionality of the invention described herein. Regardless, data processing system 1100 is capable of being implemented and/or performing any of the functionality set forth herein above, such as the tamper-respondent detector functionality discussed.

In data processing system 1100, there is a detector/computing system 1112, which may be described in the general context of computer system executing instructions, such as program modules. Generally, program modules may include routines, programs, objects, components, logic, data structures, and so on that perform particular tasks or implement particular abstract data types. One or more aspects of detector/computing system 1112 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 11, detector/computing system 1112 in data processing system 1100 is shown in the form of a general-purpose computing device. The components of detector/computing system 1112 may include, but are not limited to, one or more processors or processing units 1116, a system memory 1123, and a bus 1118 that couples various system components including system memory 1123 to processor(s) 1116.

Bus 1118 represents one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), Micro Channel Architecture (MCA), Enhanced ISA (EISA), Video Electronics Standards Association (VESA), and Peripheral Component Interconnect (PCI).

Detector/computing system 1112 may include a variety of computer system readable media. Such media may be any available media that is accessible by detector/computing system 1112, and it includes both volatile and non-volatile media, removable and non-removable media.

For instance, system memory 1123 can include computer system readable media in the form of volatile memory, such as random access memory (RAM) 1130 and/or cache memory 1132. Detector/computing system 1112 may further include other removable/non-removable, volatile/non-volatile computer system storage media. By way of example only, storage system 1134 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1118 by one or more data media interfaces. As will be further depicted and described below, memory 1123 may include at least one program product having a set (e.g., at least one) of program modules that are configured to carry out the functions of embodiments of the invention.

Program/utility 1140, having a set (at least one) of program modules 1142, may be stored in memory 1123 by way of example, and not limitation, as well as an operating system, one or more application programs, other program modules, and program data. Each of the operating system, one or more application programs, other program modules, and program data or some combination thereof, may include an implementation of a networking environment. Program modules 1142 may generally carry out the functions and/or methodologies of embodiments of the invention as described herein.

Detector/computing system 1112 may electrically connect to one or more external components, such as tamper-respondent sensor(s) 1102 and embedded tamper-respondent sensor(s) 1103 via one or more interface(s) 1122. Also, in one or more implementations, the tamper-detect process/module 1101, including the non-linear conductivity monitoring, may be provided separately, coupling to the other components of detector/computing system 1112 via bus 1118, as illustrated in FIG. 11. It should also be understood that although not shown, other hardware and/or software components could be used in conjunction with detector/computing system 1112. Examples, include, but are not limited to: microcode, device drivers, redundant processing units, etc.

The control aspects of the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of aspects of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Certain aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A tamper-respondent assembly comprising:
    at least one tamper-respondent sensor including conductive lines forming, at least in part, at least one tamper-detect network of the at least one tamper-respondent sensor;
    a detector to monitor the at least one tamper-respondent sensor, the detector applying an electrical signal to the conductive lines of the at least one tamper-respondent sensor to monitor over time for a non-linear conductivity change, where the non-linear conductivity change is indicative of a tamper event at the at least one tamper-respondent sensor; and
    wherein the detector monitors a second harmonic of the electrical signal applied to the conductive lines for the non-linear conductivity change indicative of the tamper event at the at least one tamper-respondent sensor.

2. The tamper-respondent assembly of claim 1, wherein the electrical signal has both known DC characteristics and known AC characteristics.

3. The tamper-respondent assembly of claim 1, wherein the tamper event comprises a shunt of one or more conductive lines of the conductive lines of the at least one tamper-respondent sensor, the non-linear conductivity change resulting from the shunt contacting the one or more conductive lines.

4. The tamper-respondent assembly of claim 1, wherein the at least one tamper-respondent sensor comprises at least one flexible layer, and the conductive lines are disposed on the at least one flexible layer to form, at least in part, the at least one tamper-detect network.

5. The tamper-respondent assembly of claim 1, further comprising:
    a circuit board; and
    the at least one tamper-respondent sensor comprises an embedded tamper-respondent sensor embedded within the circuit board, the conductive lines being conductive lines embedded within the circuit board.

6. The tamper-respondent assembly of claim 1, wherein the detector periodically applies the electrical signal to the conductive lines.

7. The tamper-respondent assembly of claim 1, wherein the conductive lines of the at least one tamper-respondent sensor each have a line width $W_l \leq 200$ μm.

8. The tamper-respondent assembly of claim 1, wherein the conductive lines of the at least one tamper-respondent sensor comprise metal lines or metal alloy lines.

9. A tamper-respondent assembly comprising:
    at least one electronic component;
    an enclosure surrounding, at least in part, the at least one electronic component;
    a tamper-respondent sensor associated with the enclosure and facilitating forming a secure volume about the at least one electronic component, the tamper-respondent sensor comprising conductive lines forming, at least in part, a tamper-detect network of the tamper-respondent sensor;
    a detector to monitor the tamper-respondent sensor, the detector applying an electrical signal to the conductive lines of the tamper-respondent sensor to monitor over time for a non-linear conductivity change, where the non-linear conductivity charge is indicative of a tamper event at the tamper-respondent sensor; and
    wherein the detector monitors a second harmonic of the electrical signal applied to the conductive lines for the non-linear conductive change indicative of the tamper event at the at least one tamper-respondent sensor.

10. The tamper-respondent assembly of claim 9, wherein the tamper event comprises a shunt of one or more conductive lines of the conductive lines of the tamper-respondent sensor, and the non-linear conductivity change results from the shunt contacting the one or more conductive lines.

11. The tamper-respondent assembly of claim 9, wherein the tamper-respondent sensor comprises at least one flexible layer, and the conductive lines are disposed on the at least one flexible layer to form, at least in part, the at least one tamper-detect network.

12. The tamper-respondent assembly of claim 11, wherein the tamper-respondent sensor is mounted to an inner surface of the enclosure.

13. The tamper-respondent assembly of claim 12, further comprising:
    a circuit board; and
    an embedded tamper-respondent sensor embedded within the circuit board, wherein the tamper-respondent sensor and the embedded tamper-respondent sensor together facilitate defining the secure volume about the at least one electronic component.

14. The tamper-respondent assembly of claim 9, wherein the conductive lines of the tamper-respondent sensor comprise metal lines or metal alloy lines, and the conductive lines each have a line width $W_l \leq 200$ μms.

15. A fabrication method comprising:
    fabricating a tamper-respondent assembly, the fabricating comprising:
        providing at least one tamper-respondent sensor comprising conductive lines forming, at least in part, at least one tamper-detect network of the at least one tamper-respondent sensor;
        providing a detector to monitor the at least one tamper-respondent sensor, the detector applying an electrical signal to the conductive lines of the at least one tamper-respondent sensor to monitor over time for a non-linear conductivity change, where the non-linear conductivity charge is indicative of a tamper event at the at least one tamper-respondent sensor; and wherein the detector monitors a second harmonic of the electrical signal applied to the conductive lines for the non-linear conductivity change indicative of the tamper event at the at least one tamper-respondent sensor.

16. The fabrication method of claim 15, wherein the applying by the detector comprises periodically applying the electrical signal to the conductive lines, and wherein the electrical signal has both known DC characteristics and known AC characteristics.

17. The fabrication method of claim 15, further comprising:

providing an enclosure surrounding, at least in part, at least one electronic component;

associating the at least one tamper-respondent sensor with the enclosure to facilitate forming a secure volume about the at least one electronic component;

providing a circuit board with an embedded tamper-respondent sensor embedded within the circuit board; and mounting the enclosure with the tamper-respondent sensor to the circuit board, wherein the at least one tamper-respondent sensor associated with the enclosure and the embedded tamper-respondent sensor within the circuit board together facilitate defining the secure volume about the at least one electronic component.

* * * * *